United States Patent [19]
Yukimasa et al.

[11] Patent Number: 5,677,298
[45] Date of Patent: Oct. 14, 1997

[54] BENZOXAZEPINE-2-ONE COMPOUNDS AND THEIR USE

[75] Inventors: Hidefumi Yukimasa, Nara; Masakuni Kori, Miki; Ryuichi Tozawa, Ibaraki; Yasuo Sugiyama, Kawanishi, all of Japan

[73] Assignee: Takeda Chemical Industries, Osaka, Japan

[21] Appl. No.: 696,118

[22] Filed: Aug. 13, 1996

Related U.S. Application Data

[63] Continuation of Ser. No. 312,194, Sep. 26, 1994, abandoned.

[30]     Foreign Application Priority Data

Sep. 24, 1993 [JP] Japan ................................. 5-238273
Sep. 28, 1993 [JP] Japan ................................. 5-241062

[51] Int. Cl.$^6$ ...................... A61K 31/55; C07D 267/14; C07D 303/48; A01N 43/72
[52] U.S. Cl. ...................... 514/215; 540/490; 549/549
[58] Field of Search ...................... 540/490; 514/215

[56]     References Cited

FOREIGN PATENT DOCUMENTS

| | | |
|---|---|---|
| 142361 | 5/1985 | European Pat. Off. . |
| 475706 | 3/1992 | European Pat. Off. . |
| 567026 | 10/1993 | European Pat. Off. . |
| 57-35576 | 2/1982 | Japan . |
| WO 93/07129 | 12/1992 | Japan . |
| 2 075 012 | 11/1981 | United Kingdom . |
| WO 92/15579 | 9/1992 | WIPO . |

OTHER PUBLICATIONS

Biller J. Medicinal Chemistry 31, 1869–1871 (1988), "Isoprenoid (Phosphinylmethyl)phosphonates as Inhibitors of Squalene Synthetase".

Masuoka Chem. Pharm. Bull. 34, 140–149(1986), "Synthesis of Medium–Sized Heterocycles Using an Interamolecular Michael Reaction".

Baxter, J. Biol. Chem 268, 24832 (1993).

Hoeg, T.A.M.A. 258 3532 (1987).

*Primary Examiner*—Mark L. Berch
*Attorney, Agent, or Firm*—Foley & Lardner

[57]     ABSTRACT

Disclosed is a squalene synthetase inhibitor which comprises the compound represented by the formula (I)

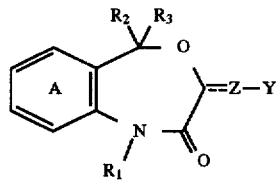

wherein $R_1$ stands for H or an optionally substituted hydrocarbon group; $R_2$ and $R_3$ independently stand for H, an optionally substituted alkyl group, an optionally substituted phenyl group or an optionally substituted aromatic heterocyclic group; Z stands for a carbon chain containing a double bond or —Z'—C(OH)— (Z' stands for a bond or a straight-chain or branched alkylene chain); the symbol ═══ stands for a double bond or a single bond; Y stands for an optionally esterified carboxyl group, an optionally substituted carbamoyl group, an optionally substituted hydroxyl group, an optionally substituted amino group or an optionally substituted heterocyclic radical having a protonizable hydrogen; X stands for O or S; G stands for O or S; and the ring A is optionally substituted, or a pharmaceutically acceptable salt thereof, and which is useful for the prophylaxis or therapy of hypercholesteremia or coronary sclerosis of mammals.

25 Claims, No Drawings

5,677,298

BENZOXAZEPINE-2-ONE COMPOUNDS AND THEIR USE

This application is a continuation of application Ser. No. 08/312,194, filed Sep. 26, 1994 abandoned.

FIELD OF THE INVENTION

This invention relates to a condensed 7-membered cyclic compound or a salt thereof, and, to a squalene synthetase inhibitor comprising same as the effective component.

BACKGROUND OF THE INVENTION

Hypercholesteremia, high blood pressure and smoking are known as three major dangerous factors of causing ischemic heart diseases. Adequate control of cholesterol concentration in blood is remarkably important for the prophylaxis or therapy of, besides these ischemic heart diseases, as well as of coronary sclerosis.

As pharmaceutical compositions for lowering cholesterol in blood, attention has been drawn to those for controlling the biosynthesis of cholesterol, besides those of inhibiting its absorption by binding bile acid including, among others, cholestyramine, colestipol (disclosed in, for example, U.S. Pat. No. 4,027,009), and those of suppressing the intestinal absorption of cholesterol by inhibiting acyl coenzyme A cholesterol acyl transferase (ACAT) including melinamide (disclosed in French Patent No.1476569). As pharmaceutical preparations for controlling the biosynthesis of cholesterol, lovastatin (disclosed in U.S. Pat. No. 4,231,938), simvastatin (disclosed in U.S. Pat. No. 4,444,784), pravastatin (U.S. Pat. No. 4,346,227), etc., which are capable of inhibiting especially 3-hydroxy-3-methyl glutaryl coenzyme (HMG-CoA) reductase, are provided for medicinal use. However, when HMG-CoA reductase is inhibited, not only the biosynthesis of cholesterol but the biosynthesis of some other components such ubiquinone, dolichol and heme A, which are necessary for the living body, is also inhibited, so that occurrences of undesirable side effects to be caused thereby are feared.

Squalene synthetase is an enzyme taking part in the essential step of new cholesterol biosynthetic route. And, this enzyme is an enzyme forming squalene catalyzing the reductive dimerization of two molecules of farnesyl pyrophosphoric acid.

On the other hand, the compounds expected as inhibitors of cholesterol biosynthesis by inhibiting squalene synthetase are disclosed in Journal of Medicinal Chemistry, Vol. 51, No. 10, pp. 1869–1871, 1988, Japanese published unexamined patent application No. H1-213288/1989(JPA H1(1989)-213288), JPA H2(1990)-101088, JPA H2(1990)-235820, JPA H2(1990)-235821, JPA H3(1991)-20226, JPA H3(1991)-68591, JPA H3(1991)-148288 and U.S. Pat. No. 5,019,390, U.S. Pat. No. 5,135,935, WO9215579, WO9309155 and WO9313096.

And, various compounds showing antifungal action by inhibiting the synthesis of squalene have been known (JPA H4(1992)-279589, EP-475706, EP-494622, EP-503520, among others).

Among 4,1-benzoxazepine derivatives, in 4,1-benzoxazepin-2-one derivatives in which 2-position is substituted with ketone group, those in which one of the hydrogen atoms at 3-position is replaced with a different substituent, are disclosed in JPA S57(1982)-345765 and Chem. Pharm. Bull., 34, 140 (1986).

OBJECT OF THE INVENTION

Ubiquinone, dolichol and heme A have been known as being synthesized from farnesyl pyrophosphate along the cholesterol biosynthesis pathway. Therefore, for avoiding occurrence of side effects due to loss of these substances, it is desirable to inhibit enzyme systems subsequent to farnesyl pyrophosphate, especially squalene synthetase, in the cholesterol biosynthetic pathway.

SUMMARY OF THE INVENTION

The present inventors have, taking the above-mentioned circumstances into consideration, made diligent research work, and found that 4,1-benzoxazepin-2-one derivatives have an excellent action of inhibiting squalene synthetase, and further have an antifungal action as well, thus the present invention being accomplished.

More specifically, the present invention is to provide (1) a condensed 7-membered cyclic compound represented by the formula (I)

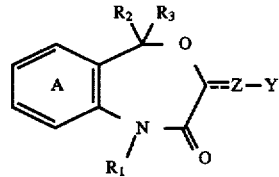

wherein $R_1$ stands for H or an optionally substituted hydrocarbon group; $R_2$ and $R_3$ independently stand for H, an optionally substituted alkyl group, an optionally substituted phenyl group or an optionally substituted aromatic heterocyclic group; Z stands for a carbon chain containing a double bond or —Z'—C(OH)—(Z' stands for a bond or a straight-chain or branched alkylene chain); the symbol ═══ stands for a double bond or a single bond; Y stands for an optionally esterified carboxyl group, an optionally substituted carbamoyl group, an optionally substituted hydroxyl group, an optionally substituted amino group or an optionally substituted heterocyclic radical having protonizable hydrogen; and the ring A is optionally substituted or a salt thereof, and (2) a squalene synthetase inhibitor comprising the condensed 7-membered cyclic compound represented by the formula (I) or a salt thereof.

Further, the present invention is to provide a method of producing a novel compound represented by the formula (I) or a salt thereof.

DETAILED DESCRIPTION OF THE INVENTION

In the above formulae (I), as the hydrocarbon group of the "optionally substituted hydrocarbon groups" shown by $R_1$, mention is made of aliphatic chain-like hydrocarbon groups, alicyclic hydrocarbon groups and aryl groups, etc., among them, aliphatic chain-like hydrocarbon groups being preferable.

As the aliphatic chain-like hydrocarbon groups of said hydrocarbon groups, mention is made of, for example, straight-chain or branched aliphatic hydrocarbon groups, such as alkyl group, alkenyl group, alkynyl group, etc., among them, alkyl groups being preferable. As the alkyl group, mention is made of, for example, $C_{1-7}$ alkyl such as methyl, ethyl, n-propyl, isopropyl, n-butyl, isobutyl, sec-butyl, tert-butyl, n-pentyl, isopentyl, neopentyl, 1-methylpropyl, n-hexyl, isohexyl, 1,1-dimethylbutyl, 2,2-dimethylbutyl, 3,3-dimethylbutyl, 3,3-dimethylpropyl, 2-ethylbutyl, n-heptyl, etc., and, among them, $C_{3-5}$ alkyl groups such as n-propyl, isopropyl, isobutyl, neopentyl, etc. are preferable, further, isobutyl, neopentyl being preferable.

As the said alkenyl group, mention is made of, for example, $C_{2-6}$ alkenyl such as vinyl, allyl, isopropenyl, 2-methylallyl, 1-propenyl, 2-methyl-1-propenyl, 2-methyl-2-propenyl, 1-butenyl, 2-butenyl, 3-butenyl, 2-ethyl-1-butenyl, 2-methyl-2-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl, 5-hexenyl, etc., and, among them, vinyl, allyl, isopropenyl, 2-methylallyl, 2-methyl-1-propenyl, 2-methyl-2-propenyl, 3-methyl-2-butenyl, etc. are especially preferable. As the said alkynyl group, mention is made of, for example, $C_{2-6}$ alkynyl such as ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, etc., and, among them, ethynyl, 1-propynyl, 2-propynyl, etc. are especially preferable.

Examples of the alicyclic hydrocarbon groups of said hydrocarbon group include saturated or unsaturated alicyclic hydrocarbon groups such as cycloalkyl group, cycloalkenyl group, cycloalkadienyl group, etc. As said cycloalkyl group, $C_{3-9}$ cycloalkyl groups are preferable, for example, cyclopropyl, cyclobutyl, cyclopentyl, cyclohexyl, cycloheptyl, cyclooctyl, cyclononyl, etc. are mentioned, and, among them, $C_{3-6}$ cycloalkyl groups such as cyclopropyl, cyclobutyl, cyclopentyl, cyclohexyl, etc. are preferable. As said cycloalkenyl group, mention is made of, for example, 2-cyclopenten-1-yl, 3-cyclopenten-1-yl, 2-cyclohexen-1-yl, 3-cyclohexen-1-yl, 1-cyclobuten-1-yl, 1-cyclopenten-1-yl, etc. As said cycloalkadienyl group, mention is made of, for example, 2,4-cyclopentadien-1-yl, 2,4-cyclohexadien-1-yl, 2,5-cyclohexadien-1-yl, etc.

As the aryl group of said hydrocarbon group, mention is made of mono-cyclic or condensed polycyclic aromatic hydrocarbon groups, for example, phenyl, naphthyl, anthryl, phenanthryl, acenaphthylenyl, etc., and, among them, phenyl, 1-naphthyl, 2-naphthyl, etc. are especially preferable.

As substituents of the "optionally substituted hydrocarbon groups" shown by $R_1$, mention is made of optionally substituted aryl groups, optionally substituted cycloalkyl groups or cycloalkenyl groups, optionally substituted heterocyclic groups, optionally substituted amino groups, optionally substituted hydroxyl groups, optionally substituted thiol groups, halogen (e.g. fluorine, chlorine, bromine, iodine), etc., and, the hydrocarbon group shown by $R_1$ is optionally substituted with 1 to 5 (preferably 1 to 3) of these substituents at any possible position. As aryl groups of said optionally substituted aryl groups, mention is made of phenyl, naphthyl, anthryl, phenanthryl, acenaphthylenyl, etc., and, among them, phenyl, 1-naphthyl and 2-naphthyl are preferable. As substituents of said optionally substituted aryl, mention is made of $C_{1-3}$ alkoxy groups (e.g. methoxy, ethoxy, propoxy, etc.), halogen atoms (e.g. fluorine, chlorine, bromine, iodine), $C_{1-3}$ alkyl groups (e.g. methyl, ethyl, propyl, etc.), and the aryl is optionally substituted with one or two of optional ones of them. As cycloalkyl groups of said optionally substituted cycloalkyl groups, mention is made of $C_{3-7}$ cycloalkyl groups including cyclopropyl, cyclobutyl, cyclopentyl, cyclohexyl, cycloheptyl, etc. The kinds and number of the substituents of said optionally substituted cycloalkyl groups are substantially the same as those in the case of the above-mentioned aryl groups. As cycloalkenyl groups of said optionally substituted cycloalkenyl groups, mention is made of, among others, $C_{3-6}$ cycloalkenyl groups such as cyclopropenyl, cyclobutenyl, cyclopentenyl, cyclohexenyl, etc. The kinds and number of the substituents of said optionally substituted cycloalkenyl groups are substantially the same as those in the case of the above-mentioned optionally substituted aryl groups. As heterocyclic groups of said optionally substituted heterocyclic groups, mention is made of, aromatic heterocyclic groups having, as the atoms (cyclic atoms) constituting the cyclic system, at least one hetero-atom selected from oxygen, sulfur and nitrogen, and saturated or unsaturated non-aromatic heterocyclic groups (aliphatic heterocyclic groups), preferably aromatic heterocyclic groups. As said aromatic heterocyclic groups, mention is made of aromatic mono-cyclic heterocyclic groups (e.g. furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, triazinyl, etc.) and aromatic condensed heterocyclic groups. (e.g. benzofuranyl, isobenzofuranyl, benzo[b]thienyl, indolyl, isoindolyl, 1H-indazolyl, benzimidazolyl, benzoxazolyl, 1,2-benzoisoxazolyl, benzothiazolyl, 1,2-benzoisothiazolyl, 1H-benzotriazolyl, quinolyl, isoquinolyl, cinnolinyl, quinazolinyl, quinoxalinyl, phthalazinyl, naphthyridinyl, purinyl, pteridinyl, carbazolyl, α-carbolinyl, β-carbolinyl, γ-carbolinyl, acrydinyl, phenoxazinyl, phenothiazinyl, phenazinyl, phenoxathiinyl, thianthrenyl, phenanthridinyl, phenanthrolinyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, 1,2,4-triazolo[4,3-b]pyridazinyl, etc.), and, among them, furyl, thienyl, indolyl, isoindolyl, pyrazinyl, pyridyl, pyrimidinyl, etc. are preferable. Examples of said non-aromatic heterocyclic groups include oxiranyl, azetidinyl, oxetanyl, thietanyl, pyrrolidinyl, tetrahydrofuryl, thiolanyl, piperidyl, tetrahydropyranyl, morpholinyl, thiomorpholinyl, piperazinyl, etc. As substituents of said optionally substituted heterocyclic groups, mention is made of $C_{1-3}$ alkyl groups (e.g. methyl, ethyl, propyl, etc.). Examples of substituents of said optionally substituted amino groups, optionally substituted hydroxyl groups and optionally substituted thiol groups include lower ($C_{1-3}$) alkyl (e.g. methyl, ethyl, propyl, etc.). And, when the hydrocarbon groups in the optionally substituted hydrocarbon groups shown by $R_1$ are alicyclic hydrocarbon groups or aryl group, they may have, as substituents, $C_{1-3}$ alkyl groups (e.g. methyl, ethyl, propyl, etc.)

As the alkyl groups of "optionally substituted alkyl groups" shown by $R_2$ and $R_3$, mention is made of $C_{1-6}$ lower alkyl groups (e.g. methyl, ethyl, n-propyl, isopropyl, butyl, isobutyl, sec-butyl, tert-butyl, pentyl, isopentyl, neopentyl, hexyl, isohexyl, etc.), and, among them, $C_{1-4}$ alkyl groups including methyl, ethyl, propyl, isopropyl, butyl and t-butyl are preferable. As the substituents of said optionally substituted lower alkyl groups, mention is made of halogen (e.g. fluorine, chlorine, bromine, iodine), $C_{1-4}$ lower alkoxy groups (e.g. methoxy, ethoxy, propoxy, isopropoxy, butoxy, t-butoxy, etc.).

As substituents of "optionally substituted phenyl groups" shown by $R_2$ and $R_3$, mention is made of halogen atoms (e.g. fluorine, chlorine, bromine, iodine), an optionally substituted lower alkyl, an optionally substituted lower alkoxy, an optionally substituted hydroxyl group, nitro group, cyano group, etc., and the phenyl group may be preferably substituted with 1 to 3 substituents (preferably 1 to 2) of these substituents at any possible positions. As the lower alkyl, mention is made of, for example, $C_{1-4}$ alkyl groups including methyl, ethyl, n-propyl, isopropyl, n-butyl, isobutyl, sec-butyl, tert-butyl, etc., and especially methyl and ethyl are preferable. As the lower alkoxy, mention is made of $C_{1-4}$ alkoxy groups including methoxy, ethoxy, n-propoxy, isopropoxy, n-butoxy, isobutoxy, sec-butoxy, tert-butoxy, etc., and especially methoxy and ethoxy are preferable. As substituents of said optionally substituted lower alkyl groups or optionally substituted lower alkoxy groups, mention is made of halogen atoms (e.g. fluorine, chlorine, bromine, iodine, etc.), and one to five of these may optionally substituted at an optional possible position. As substituents at said optionally substituted hydroxyl group, mention is made of, for example, $C_{1-4}$ alkyl groups (e.g. methyl, ethyl, propyl, isopropyl, butyl, t-butyl, etc.), $C_{3-6}$ cycloalkyl groups (cyclopropyl, cyclobutyl, cyclopentyl, cyclohexyl, etc.), aryl groups (e.g. phenyl, 1-naphthyl, 2-naphthyl, etc.), aralkyl groups (e.g. benzyl, phenethyl, etc.). And, these substituents may form a ring together with the adjacent substituents to each other, for example, the following is mentioned:

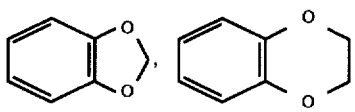

Said ring may be substituted with a lower ($C_{1-3}$) alkyl (e.g. methyl, ethyl, propyl, isopropyl, etc.) and the like.

As aromatic heterocyclic groups of the "optionally substituted aromatic heterocyclic groups" shown by $R_2$ and $R_3$, mention is made of aromatic heterocyclic groups described in detail referring to $R_1$, and, among them, furyl, thienyl, indolyl, isoindolyl, pyrazinyl, pyridyl, pyrimidyl, imidazolyl, etc. are preferable. As substituents of said aromatic heterocyclic groups, mention is made of $C_{1-3}$ alkyl groups (e.g. methyl, ethyl, propyl, etc.).

Among the above-exemplified groups represented by $R_2$ and $R_3$, optionally substituted phenyl groups, preferably substituted phenyl groups are preferable, with greater preference given to a phenyl group substituted with halogen, lower alkoxy, etc.

As the "carbon chain containing double bond" shown by Z, mention is made of, preferably, those in which the carbon number constituting the straight-chain portion ranges from 1 to 7, more preferably 1 to 4, and they may optionally have side chains. While the double bond at said carbon chain is contained in the straight-chain portion and/or branched chain portion, it is contained preferably in the straight-chain portion. Number of the double bond contained in said carbon chain is not restricted as far as possible, it ranges preferably from 1 to 2.

Examples of carbon chains containing said double bond include methine, vinylene, propenylene, butenylene, butadienylene, methylpropenylene, ethylpropenylene, propylpropenylene, methylbutenylene, ethylbutenylene, propylbutenylene, methylbutadienylene, ethylbutadienylene, propylbutadienylene, pentenylene, hexenylene, heptenylene, pentadienylene, hexadienylene and heptadienylene, preferably methine, vinylene, propenylene, butenylene and butadienylene.

Examples of the "straight-chain or branched alkylene chain" shown by Z' include straight-chain or branched $C_{1-6}$ alkylene chain, more specifically, divalent ones such as methylene, ethylene, trimethylene, tetramethylene, pentamethylene, hexamethylene, heptamethylene, propylene, ethylmethylene, ethylethylene, propylethylene, butylethylene, methyltetramethylene and methyltrimethylene, and, preferably, $C_{1-3}$ ones such as methylene, ethylene, trimethylene and propylene.

As the "optionally esterified carboxyl group" shown by Y, mention is made of lower alkoxycarbonyl (e.g. methoxycarbonyl, ethoxycarbonyl, propoxycarbonyl, isopropoxycarbonyl, butoxycarbonyl, tert-butoxycarbonyl, sec-butoxycarbonyl, pentyloxycarbonyl, isopentyloxycarbonyl, neopentyloxycarbonyl, tert-pentyloxycarbonyl, etc.), aryloxycarbonyl (e.g. phenoxycarbonyl, 1-naphthoxycarbonyl, benzyloxycarbonyl, etc.) etc., and, among them, carboxyl group, methoxycarbonyl and ethoxycarbonyl are preferable.

Examples of substituents of the "optionally substituted carbamoyl group" shown by Y include optionally substituted lower ($C_{1-6}$) alkyl (e.g. methyl, ethyl, n-propyl, isopropyl, butyl, isobutyl, sec-butyl, tert-butyl, pentyl, isopentyl, neopentyl, hexyl, isohexyl, etc.), optionally substituted $C_{3-6}$ cycloalkyl groups (e.g. cyclopropyl, cyclobutyl, cyclopentyl, cyclohexyl, etc.), optionally substituted aryl group (e.g. phenyl, 1-naphthyl, 2-naphthyl, etc.), optionally substituted aralkyl groups (e.g. benzyl, phenethyl, etc.), and, one or two of these substituents may independently substituted. As substituents at said optionally substituted lower ($C_{1-6}$) alkyl and optionally substituted $C_{3-6}$ cycloalkyl group, mention is made of, carboxyl group optionally esterified with a lower ($C_{1-5}$) alkyl (e.g. methyl, ethyl, propyl, isopropyl, butyl, t-butyl, pentyl, isopentyl, neopentyl, etc.), aromatic heterocyclic groups (e.g. furyl, thienyl, indolyl, isoindolyl, pyrazinyl, pyridyl, pyrimidyl, imidazolyl, etc.), amino group, hydroxyl group, phenyl group, etc., and, one to three of these substituents may independently substituted. As substituents of said optionally substituted aryl groups and optionally substituted aralkyl groups, mention is made of, halogen atoms (e.g. fluorine, chlorine, bromine, iodine), carboxyl groups optionally esterified with a lower ($C_{1-4}$) alkyl (e.g. methyl, ethyl, propyl, isopropyl, butyl, t-butyl, etc.). And, two substituents on a nitrogen atom may form a cyclic amino group taken together with the nitrogen atom. Examples of such cyclic amino group include 1-azetidinyl, 1-pyrrolidinyl, piperidino, morpholino, 1-piperazinyl, etc.

Examples of substituents of the "optionally substituted hydroxyl groups" shown by Y include lower ($C_{1-4}$) alkyl (e.g. methyl, ethyl, propyl, isopropyl, butyl, t-butyl, etc.), $C_{3-6}$ cycloalkyl groups (e.g. cyclopropyl, cyclobutyl, cyclopentyl, cyclohexyl, etc.), optionally substituted aryl groups (e.g. phenyl, 1-naphthyl, 2-naphthyl, etc.), optionally substituted aralkyl groups (e.g. benzyl, phenethyl, etc.), etc. As substituents of said optionally substituted aryl group and optionally substituted aralkyl group, mention is made of halogen atoms (e.g. fluorine, chlorine, bromine, iodine), carboxyl groups optionally esterified with lower ($C_{1-4}$) alkyl (e.g. methyl, ethyl, propyl, isopropyl, butyl, t-butyl, etc.), etc.

Examples of substituents of the "optionally substituted amino groups" shown by Y include lower ($C_{1-4}$) alkyl (e.g. methyl, ethyl, propyl, isopropyl, butyl, t-butyl, etc.), $C_{3-6}$ cycloalkyl groups (e.g. cyclopropyl, cyclobutyl, cyclopentyl, cyclohexyl, etc.), optionally substituted aryl groups (e.g. phenyl, 1-naphthyl, 2-naphthyl, etc.), optionally substituted aralkyl groups (e.g. benzyl, phenethyl, etc.), etc. As substituents of said optionally substituted aryl group and optionally substituted aralkyl group, mention is made of halogen atoms (e.g. fluorine, chlorine, bromine, iodine), carboxyl groups optionally esterified with lower ($C_{1-4}$) alkyl (e.g. methyl, ethyl, propyl, isopropyl, butyl, t-butyl, etc.), etc. And, two substituents on a nitrogen atom may form a cyclic amino group taken together with the nitrogen atom. Examples of the cyclic amino group include 1-azetidinyl, 1-pyrrolidinyl, piperidino, morpholino, 1-piperazinyl, etc.

As heterocyclic radicals of the "optionally substituted heterocyclic radical having a protonizable hydrogen" shown by Y, mention is made of 5-7 membered (preferably 5 membered) monocyclic heterocyclic radical containing at least one hetero atom selected from the group consisting of N, S and O, more preferably N-containing heterocyclic radical. Especially, tetrazol-5-yl and groups represented by the formula

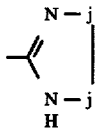

wherein i stands for —O— or —S—; j stands for >C=O, >C=S or >SO₂, (especially 2,5-dihydro-5-oxo-1,2,4-oxadiazol-3-yl, 2,5-dihydro-5-thioxo-1,2,4-oxadiazol-3-yl, 2,5-dihydro-5-oxo-1,2,4-thiadiazol-3-yl) are preferable.

Said heterocyclic radical may be protected with an optionally substituted lower alkyl (preferably $C_{1-4}$ alkyl), acyl, etc. As said optionally substituted lower alkyls, mention is made of methyl, triphenylmethyl, methoxymethyl, ethoxymethyl, p-methoxybenzyl, p-nitrobenzyl, etc. Examples of said acyl include lower ($C_{2-5}$) alkanoyl, benzoyl, etc.

Among the above-exemplified groups shown by Y, an optionally esterified carboxyl group and an optionally substituted carbamoyl group are preferable.

As substituents of the ring A, mention is made of hydroxyl group, halogen (e.g. fluorine, chlorine, bromine, iodine), nitro, cyano, $C_{1-4}$ lower alkyl groups (e.g. methyl, ethyl, n-propyl, isopropyl, n-butyl, isobutyl, sec-butyl, tert-butyl, etc.) and $C_{1-4}$ lower alkoxy group (e.g. methoxy, ethoxy, n-propoxy, isopropoxy, n-butoxy, isobutoxy, sec-butoxy, tert-butoxy, etc.), and, methyl, ethyl, methoxy, ethoxy and chlorine are preferable, especially, methoxy and chlorine are preferable. One or two of these substituents may independently substituted.

Practical examples of the compounds of this invention are disclosed as follows:

(3RS,5RS, αSR)-7-Chloro-5-(2-chlorophenyl)-1-isopropyl-2-oxo-1,2,3,5-tetrahydro-4,1-benzoxazepine-3-glycolic acid ethyl ester, (3RS,5SR,αSR)-7-Chloro-5-(2-chlorophenyl)-1-isopropyl-2-oxo-1,2,3,5-tetrahydro-4,1-benzoxazepine-3-glycolic acid ethyl ester, 7-Chloro-5-(2-chlorophenyl)-1-isobutyl-2-oxo-1,2,3,5-tetrahydro-4,1-benzoxazepine-3-glycolic acid ethyl ester, 7-Chloro-5-(2-chlorophenyl)-1-propyl-2-oxo-1,2,3,5-tetrahydro-4,1-benzoxazepine-3-glycolic acid ethyl ester, (3RS,5SR,αSR)-7-chloro-5-(2-chlorophenyl)-1-isopropyl-2-oxo-1,2,3,5-tetrahydro-4,1-benzoxazepine-3-glycolic acid, (3RS,5RS, αSR)-7-chloro-5-(2-chlorophenyl)-1-isopropyl-2-oxo-1,2,3,5-tetrahydro-4,1-benzoxazepine-3-glycolic acid, (3RS,5RS, αRS)-7-chloro-5-(2-chlorophenyl)-1-isopropyl-2-oxo-1,2,3,5-tetrahydro-4,1-benzoxazepine-3-glycolic acid, (3RS,5RS, αRS)-7-chloro-5-(2-chlorophenyl)-1-isopropyl-2-oxo-1,2,3,5-tetrahydro-4,1-benzoxazepine-3-glycolic acid, (3RS,5SR,αRS)-7-chloro-5-(2-chlorophenyl)-1-isopropyl-2-oxo-1,2,3,5-tetrahydro-4,1-benzoxazepine-3-glycolic acid, (3RS,5SR,αRS)-7-chloro-5-(2-chlorophenyl)-1-isopropyl-2-oxo-1,2,3,5-tetrahydro-4,1-benzoxazepine-3-glycolic acid ethyl ester, (3RS,5RS, αRS)-7-Chloro-5-(2-chlorophenyl)-1-isopropyl-2-oxo-1,2,3,5-tetrahydro-4,1-benzoxazepine-3-glycolic acid ethyl ester, (E)-7-Chloro-5-(2-chlorophenyl)-1-isopropyl-2-oxo-1,2,3,5-tetrahydro-4,1-benzoxazepine-3-Δ(3,Δ)-acetic acid ethyl ester, (E)-7-Chloro-5-(2-chlorophenyl)-2-oxo-1-propyl-1,2,3,5-tetrahydro-4,1-benzoxazepine-3-Δ(3,α)-acetic acid, (E)-7-Chloro-5-(2-chlorophenyl)-1-isopropyl-2-oxo-1,2,3,5-tetrahydro-4,1-benzoxazepine-3-Δ(3,α)-acetic acid, (E)-7-Chloro-5-(2-chlorophenyl)-2-oxo-1-isopropyl-1,2,3,5-tetrahydro-4,1-benzoxazepine-3-Δ(3,α)-acetic acid ethyl ester, (E)-7-Chloro-5-(2-chlorophenyl)-1-isobutyl-2-oxo-1,2,3,5-tetrahydro-4,1-benzoxazepine-3-Δ(3,α)-acetic acid ethyl ester, (E)-7-Chloro-5-(2-chlorophenyl)-1-isopropyl-2-oxo-1,2,3,5-tetrahydro-4,1-benzoxazepine-3-Δ(3,α)-acetic acid, (3RS,5SR,αRS)-7-Chloro-5-(2-chlorophenyl)-2-oxo-1-propyl-1,2,3,5-tetrahydro-4,1-benzoxazepine-3-(α-hydroxy)propionic acid ethyl ester, (3RS,5SR,αSR)-7-Chloro-5-(2-chlorophenyl)-2-oxo-1-propyl-1,2,3,5-tetrahydro-4,1-benzoxazepine-3-(α-hydroxy)propionic acid ethyl ester, (3RS,5SR,αRS)-7-Chloro-5-(2-chlorophenyl)-2-oxo-1-propyl-1,2,3,5-tetrahydro-4,1-benzoxazepine-3-(α-hydroxy)propionic acid, (3RS,5SR,αSR)-7-Chloro-5-(2-chlorophenyl)-2-oxo-1-propyl-1,2,3,5-tetrahydro-4,1-benzoxazepine-3-(α-hydroxy)propionic acid, (3RS,5SR,αRS)-7-Chloro-5-(2-chlorophenyl)-1-isopropyl-2-oxo-1,2,3,5-tetrahydro-4,1-benzoxazepine-3-(α-hydroxy)propionic acid ethyl ester, (3RS,5SR,αSR)-7-Chloro-5-(2-chlorophenyl)-1-isopropyl-2-oxo-1,2,3,5-tetrahydro-4,1-benzoxazepine-3-(α-hydroxy)propionic acid ethyl ester, (3RS,5SR,αRS)-7-Chloro-5-(2-chlorophenyl)-1-isopropyl-2-oxo-1,2,3,5-tetrahydro-4,1-benzoxazepine-3-(α-hydroxy)propionic acid, (3RS,5SR,αSR)-7-Chloro-5-(2-chlorophenyl)-1-isopropyl-2-oxo-1,2,3,5-tetrahydro-4,1-benzoxazepine-3-(α-hydroxy)propionic acid, (3RS,5SR,αRS)-7-Chloro-5-(2-chlorophenyl)-1-isobutyl-2-oxo-1,2,3,5-tetrahydro-4,1-benzoxazepine-3-(α-hydroxy)propionic acid ethyl ester, (3RS,5SR,αSR)-7-Chloro-5-(2-chlorophenyl)-1-isobutyl-2-oxo-1,2,3,5-tetrahydro-4,1-benzoxazepine-3-(α-hydroxy)propionic acid ethyl ester, (3RS,5SR,αRS)-7-Chloro-5-(2-chlorophenyl)-1-isobutyl-2-oxo-1,2,3,5-tetrahydro-4,1-benzoxazepine-3-(α-hydroxy)propionic acid, (3RS,5SR,αSR)-7-chloro-5-(2-chlorophenyl)-1-isobutyl-2-oxo-1,2,3,5-tetrahydro-4,1-benzoxazepine-3-(α-hydroxy)propionic acid, N-[(3RS,5SR,αSR)-7-Chloro-5-(2-chlorophenyl)-1-isopropyl-2-oxo-1,2,3,5-tetrahydro-4,1-benzoxazepine-3-glycolyl]aminoacetic acid ethyl ester, N-[(3RS,5SR,αSR)-7-chloro-5-(2-chlorophenyl)-1-isopropyl-2-oxo-1,2,3,5-tetrahydro-4,1-benzoxazepine-3-glycolyl]aminoacetic acid, N-[(E)-7-Chloro-5-(2-chlorophenyl)-1-isopropyl-2-oxo-1,2,3,5-tetrahydro-4,1-benzoxazepine-Δ(3,α)-acetyl]aminoacetic acid ethyl ester, N-[(E)-7-chloro-5-(2-chlorophenyl)-1-isopropyl-2-oxo-1,2,3,5-tetrahydro-4,1-benzoxazepine-Δ(3,α)-acetyl]aminoacetic acid, N-[(E)-7-Chloro-5-(2-chlorophenyl)-2-oxo-1-propyl-1,2,3,5-tetrahydro-4,1-benzoxazepine-Δ(3,α)-acetyl]aminoacetic acid ethyl ester, N-[(E)-7-Chloro-5-(2-chlorophenyl)-2-oxo-1-propyl-1,2,3,5-tetrahydro-4,1-benzoxazepine-Δ(3,α)-acetyl]aminoacetic acid, N-[(E)-7-Chloro-5-(2-chlorophenyl)-1-isobutyl-2-oxo-1,2, 3,5-tetrahydro-4,1-benzoxazepine-Δ(3,α)-acetyl] aminoacetic acid ethyl ester, N-[(E)-7-Chloro-5-(2-chlorophenyl)-1-isobutyl-2-oxo-1,2, 3,5-tetrahydro-4,1-benzoxazepine-Δ(3,α)-acetyl] aminoacetic acid, (E)-7-Chloro-5-(2,3-dimethoxyphenyl)-1-isobutyl-2-oxo-1, 2,3,5-tetrahydro-4,1-benzoxazepine-Δ(3,α)-acetic acid, (E)-7-Chloro-5-(2,4-dimethoxyphenyl)-1-isobutyl-2-oxo-1, 2,3,5-tetrahydro-4,1-benzoxazepine-Δ(3,α)-acetic acid, (E)-7-Chloro-5-(2,3-dimethoxyphenyl)-1-neopentyl-2-oxo-1,2,3,5-tetrahydro-4,1-benzoxazepine-Δ(3,α)-acetic acid, (E)-7-Chloro-5-(2,4-dimethoxyphenyl)-1-neopentyl-2-oxo-1,2,3,5-tetrahydro-4,1-benzoxazepine-Δ(3,α)-acetic acid, (E)-7-Chloro-5-(2,3-dimethoxyphenyl)-2-oxo-1-propyl-1,2, 3,5-tetrahydro-4,1-benzoxazepine-Δ(3,α)-acetic acid, (E)-7-Chloro-5-(2,4-dimethoxyphenyl)-2-oxo-1-propyl-1,2, 3,5-tetrahydro-4,1-benzoxazepine-Δ(3,α)-acetic acid, (E)-7-Chloro-5-(3-hydroxy-2-methoxyphenyl)-1-isobutyl-2-oxo-1,2,3,5-tetrahydro-4,1-benzoxazepine-Δ(3,α)-acetic acid, (E)-7-Chloro-5-(4-hydroxy-2-methoxyphenyl)-1-isobutyl-2-oxo-1,2,3,5-tetrahydro-4,1-benzoxazepine-Δ(3,α)-acetic acid, (E)-7-Chloro-5-(3-hydroxy-2-methoxyphenyl)-1-neopentyl-2-oxo-1,2,3,5-tetrahydro-4,1-benzoxazepine-Δ(3,α)-acetic acid, (E)-7-Chloro-5-(4-hydroxy-2-methoxyphenyl)-1-neopentyl-2-oxo-1,2,3,5-tetrahydro-4,1-benzoxazepine-Δ(3,α)-acetic acid, (E)-7-Chloro-5-(3-hydroxy-2-methoxyphenyl)-2-oxo-1-propyl-1,2,3,5-tetrahydro-4,1-benzoxazepine-Δ(3,α)-acetic acid, (E)-7-Chloro-5-(4-hydroxy-2-methoxyphenyl)-2-oxo-1-propyl-1,2,3,5-tetrahydro-4,1-benzoxazepine-Δ(3,α)-acetic acid, (E)-7-Chloro-5-(3-ethoxy-2-methoxyphenyl)-2-oxo-1-propyl-1,2,3,5-tetrahydro-4,1-benzoxazepine-Δ(3,α)-acetic acid, (E)-7-Chloro-5-(4-ethoxy-2-methoxyphenyl)-2-oxo-1-propyl-1,2,3,5-tetrahydro-4,1-benzoxazepine-Δ(3,α)-acetic acid, (E)-7-Chloro-5-(3-ethoxy-2-methoxyphenyl)-1-isobutyl-2-oxo-1,2,3,5-tetrahydro-4,1-benzoxazepine-Δ(3,α)-acetic acid, (E)-7-Chloro-5-(4-ethoxy-2-methoxyphenyl)-1-isobutyl-2-oxo-1,2,3,5-tetrahydro-4,1-benzoxazepine-Δ(3,α)-acetic acid, (E)-7-Chloro-5-(3-ethoxy-2-methoxyphenyl)-1-neopentyl-2-oxo-1,2,3,5-tetrahydro-4,1-benzoxazepine-Δ(3,α)-acetic acid, (E)-7-Chloro-5-(4-ethoxy-2-methoxyphenyl)-1-neopentyl-2-oxo-1,2,3,5-tetrahydro-4,1-benzoxazepine-Δ(3,α)-acetic acid, (E)-7-Chloro-5-(2-chloro-4-methoxyphenyl)-1-isobutyl-2-oxo-1,2,3,5-tetrahydro-4,1-benzoxazepine-Δ(3,α)-acetic acid, (E)-7-Chloro-5-(2-chloro-4-methoxyphenyl)-1-neopentyl-2-oxo-1,2,3,5-tetrahydro-4,1-benzoxazepine-Δ(3,α)-acetic acid, (E)-7-Chloro-5-(2-methoxyphenyl)-1-isobutyl-2-oxo-1,2,3, 5-tetrahydro-4,1-benzoxazepine-Δ(3,α)-acetic acid, (E)-7-Chloro-5-(2-methoxyphenyl)-1-neopentyl-2-oxo-1,2, 3,5-tetrahydro-4,1-benzoxazepine-Δ(3,α)-acetic acid, and (E)-7-Chloro-5-(2-methoxyphenyl)-2-oxo-1-propyl-1,2,3,5-tetrahydro-4,1-benzoxazepine-Δ(3,α)-acetic acid.

As salts of the compound (I), mention is made of pharmaceutically acceptable ones, for example, inorganic salts such as hydrochloride, hydrobromide, sulfate, nitrate, phosphate, etc., organic salts such as acetate, tartrate, citrate, fumarate, maleate, toluenesulfonate, methanesulfonate, etc., metal salts such as sodium salt, potassium salt, calcium salt, aluminum salt, and salts with a base such as triethylamine salt, guanidine salt, ammonium salt, hydrazine salt, quinine salt, cinchonine salt, etc.

The method of producing the compound of this invention is described below.

Among compounds represented by the formula (I), the compound represented by the formula (Ia)

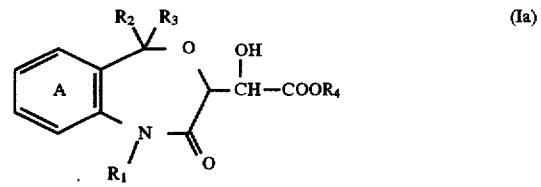

wherein $R_4$ shows the alkyl portion of the esterified carboxyl group defined by Y, and other symbols are of the same meaning as defined in the foregoing can be produced by the following process:

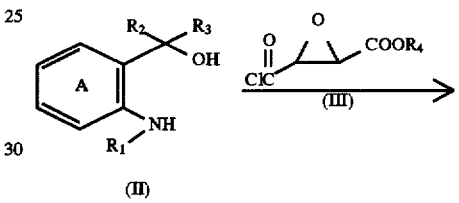

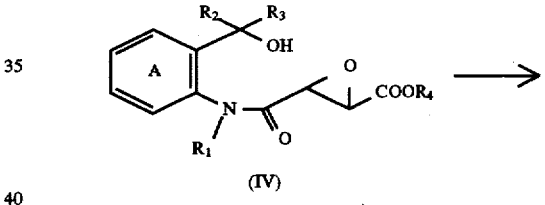

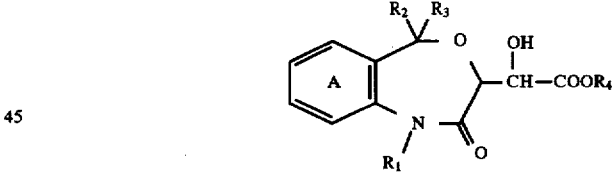

wherein symbols are of the same meaning as defined above.

The method of producing the compound represented by the formula (IV) by allowing the compound represented by the formula (II) to react with the compound represented by the formula (III) comprises acylation of amino group, which can be conducted easily by a per se known method. More specifically, the reaction can be conducted in a solvent, for example, ethers such as diethyl ether, tetrahydrofuran, dioxane, etc., halogen type solvents such as dichloromethane, dichloroethane, chloroform, carbon tetrachloride, etc., hydrocarbons such as benzene, toluene, hexane, heptane, etc., dimethylformamide, dimethyl sulfoxide, and, when necessary, in the presence of water and a base (e.g. an organic base such as 4-dimethylaminopyridine, triethylamine, triethylenediamine, tetramethylethylenediamine, etc., an inorganic base such as sodium hydrogencarbonate, potassium hydrogencarbonate, sodium carbonate, potassium carbonate, sodium hydroxide, potassium hydroxide, etc.

sodium hydride, potassium hydride), etc. Relative to one mole of the compound represented by the formula (II), the acid chloride represented by the formula (III) is employed usually in an amount of 1 to 10 moles, preferably about 1 to 3 moles. The reaction time ranges usually from about 1 to 48 hours, preferably about 5 to 10 hours. The reaction temperatures range from -50° to 100° C., preferably from 0° to 50° C.

The method of producing a compound represented by the formula (Ia) from a compound represented by the formula (IV) can be conducted in a solvent, for example, an ether type solvent such as diethyl ether, tetrahydrofuran, dioxane, etc.; a halogen type solvent such as dichloromethane, dichloroethane, chloroform, carbon tetrachloride, etc.; a hydrocarbon type solvent such as benzene, toluene, hexane, heptane, etc.; an alcohol type solvent such as methanol, ethanol, propanol, etc.; dimethylformamide, dimethyl sulfoxide, etc., and, upon necessity, in the presence of a base (e.g. an organic base such as 4-dimethylaminopyridine, triethylamine, triethylenediamine, tetramethylethylenediamine, etc. or, e.g. sodium hydrogencarbonate, potassium hydrogencarbonate, sodium carbonate, potassium carbonate). The reaction time ranges from one hour to 24 hours, preferably from 5 hours to 20 hours. The reaction temperatures roughly range from 0° to 100° C., preferably from 20° to 50° C.

The compound represented by the formula (II) employable as a starting material can be synthesized by the method described in D. A. Walsh. Synthesis. 677 (1980) or methods referred to in said literature reference, or methods analogous thereto.

Among the compounds represented by the formula (I), production of a compound represented by the formula (Ib)

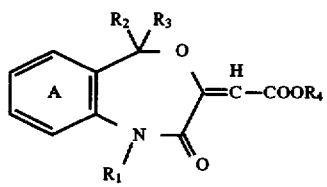

wherein symbols are of the same meaning as defined above] can be carried out by subjecting the hydroxyl group of the compound represented by the formula (Ia) to methanesulfonylation or toluenesulfonylation. The reaction itself is a conventional one, and the object compound can be produced by substantially the same method as that for producing the compound represented by the formula (IV) from the compound represented by the formula (II) and the compound represented by the formula (III). Subsequently, thus methanesulfonylated or toluenesulfonylated compounds can be subjected to reaction in a solvent, for example, an ether type solvent such as diethyl ether, tetrahydrofuran, dioxane, etc.; a halogen type solvent such as dichloromethane, dichloroethane, chloroform, carbon tetrachloride, etc.; and a hydrocarbon type solvent such as benzene, toluene, hexane, heptane, etc.; dimethylformamide, dimethyl sulfoxide, etc., and, upon necessity, in the presence of a base (for example, an organic base such as 4-dimethylaminopyridine, triethylamine, triethylenediamine, tetramethylethylenediamine, etc.; an inorganic base such as sodium hydrogencarbonate, potassium hydrogencarbonate, sodium carbonate, potassium carbonate, sodium hydroxide, potassium hydroxide, etc.; sodium hydride, potassium hydride, sodium methoxide, sodium ethoxide, sodium hydride, sodium acetate, potassium acetate, sodium propionate, cesium propionate, potassium tert-butoxide) etc.

The amount of the base ranges from 1 to 10 molar equivalents, preferably about from 1 to 2 molar equivalents relative to one mole of the methanesulfonylated or toluenesulfonylated compound. The reaction time usually ranges from one to 24 hours, preferably from 5 to 10 hours, and the reaction temperatures range from 0° to 200° C., preferably from 50° to 100° C. Among the compounds of the formula (I), a compound represented by the formula (Ic)

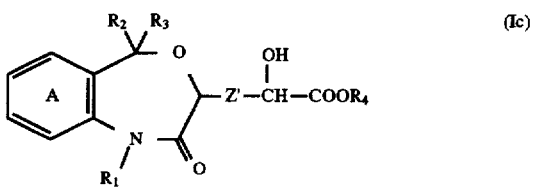

wherein each symbol has the same meaning as defined above can be produced by converting a compound represented by the formula (V)

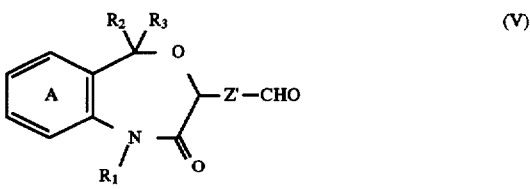

wherein each symbol is of the same meaning as defined above, to cyanohydrin, then by subjecting the cyano group to hydrolysis. The production of the cyanohydrin can be conducted by allowing the compound represented by the formula (V) to react in acetone cyanohydrin, and, upon necessity, in the presence of a base (for example, 4-dimethylaminopyridine, triethylamine, triethylenediamine, etc.). The reaction time ranges from 10 minutes to 5 hours, preferably from 30 minutes to 2 hours, and the reaction temperatures range from 0° to 100° C., preferably about 20° to 50° C. The amount of the base to be employed ranges from 0.1 to 3 molar equivalents, preferably from about 0.2 to 0.5 molar equivalents, relative to one mole of the compound represented by the formula (V). Hydrolysis of thus-obtained cyanohydrin can be conducted by a per se known method, in the presence of, as a solvent, an alcohol type solvent such as methanol, ethanol or propanol, and an acid((e.g. hydrogen chloride, sulfuric acid). The reaction temperature ranges from 30° to 150° C., preferably from about 50° to 100° C. The reaction time ranges from 10 minutes to 5 hours, preferably from about 30 minutes to one hour.

Among the compounds of the formula (I), a compound of the formula (Id)

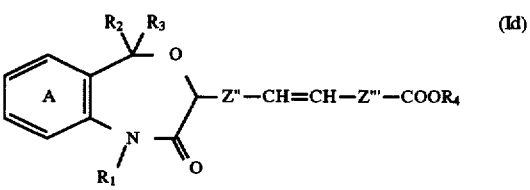

wherein Z" and Z'" respectively stand for a carbon chain optionally containing a bond or a double bond, and other symbols are of the same meaning as defined above can be produced by allowing a compound represented by the formula (V')

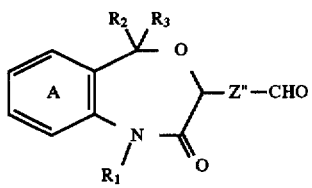

(V')

wherein each symbol is of the same meaning as defined above] to react with a compound represented by the formula (VI)

Ph₃P=CH—Z'"—COOR₄     (VI)

wherein symbols are of the same meaning as defined above. The reaction is conducted in a solvent, for example, an ether type solvent such as diethyl ether, tetrahydrofuran, dioxane, etc., a halogen type solvent such as dichloromethane, dichloroethane, chloroform, carbon tetrachloride, etc., a hydrocarbon type solvent such as benzene, toluene, hexane, heptane, etc., dimethylformamide, dimethyl sulfoxide, etc., the amount of the compound represented by the formula (VI) being 1 to 10 molar equivalents, preferably about 1 to 3 molar equivalents relative to one mole of the compound of the formula (V') at temperatures ranging from 50° to 200° C., preferably from about 80° to 100° C. for the period ranging from one to 24 hours, preferably from about 3 to 10 hours.

Among the compounds of the formula (I), production of a compound of the formula (Ie)

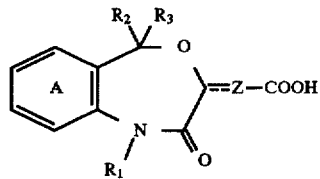

(Ie)

wherein symbols are of the same meaning as defined above can be conducted by subjecting a compound of the formula (Ia), (Ib), (Ic), (Id) or (Ij) to be described later to reaction in a solvent, for example, water or an alcohol type solvent such as methanol, ethanol, propanol, etc. or an ether type solvent such as tetrahydrofuran, dioxane, etc., in the presence of a base (e.g. sodium hydrogencarbonate, potassium hydrogencarbonate, sodium carbonate, potassium carbonate, sodium hydroxide, potassium hydroxide, barium hydroxide, etc.), an acid (hydrochloric acid, sulfuric acid, nitric acid, etc.) for one to 24 hours, preferably from about 2 to 3 hours at temperatures ranging from 0° to 100° C., preferably from about 20° to 50° C.

Among the compounds of the formula (I), a compound of the formula (If)

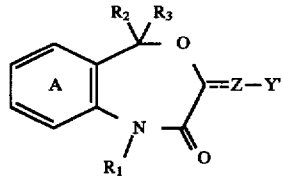

(If)

wherein Y' stands for optionally substituted carbamoyl group defined by Y, and other symbols are of the same meaning as defined above] can be produced by subjecting the compound of the formula (Ie) to condensation with amine having the same substituents as those of optionally substituted carbamoyl group. For example, in a solvent including an ether-type one such as diethyl ether, tetrahydrofuran, dioxane, etc., a hydrocarbon type solvent such as benzene, toluene, hexane, heptane, etc., a halogen type solvent such as dichloromethane, chloroform, etc., acetonitrile, dimethylformamide solvent, usually 1 to 5 moles of amine having the same substituents as those of the optionally substituted carbamoyl group, preferably about 1 to 1.5 moles, relative to 1 mole of the compound of the formula (Ie). The reaction temperatures range from 0° to 100° C., preferably from about 20° to 50° C. The reaction time ranges from 1 to 24 hours, preferable about 2 to 5 hours. The condensing agent then employed includes diethyl cyanophosphonate, dicyclohexylcarbodiimide, etc., the amount of which being usually 1 to 5 moles, preferably 1 to 2 moles, relative to 1 mole of the compound of the formula (Ie).

Among the compounds of the formula (I), production of a compound of the formula (Ig)

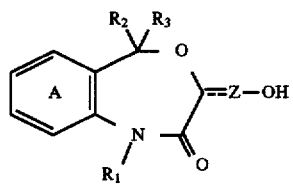

(Ig)

wherein symbols are of the same meaning as defined above can be conducted by subjecting a compound shown by the formula (Ia), the formula (Ib), the formula (Ic), the formula (Id) or (Ij) described later to reduction with lithium aluminum hydride in an ether type solvent such as diethyl ether, tetrahydrofuran, dioxane, etc. Relative to one mole of the compound shown by the formula (Ia), the formula (Ib), the formula (Ic), the formula (Id) or the formula (Ij), lithium aluminum hydride is used in an amount ranging from 0.1 to 3 moles, preferably from about 0.3 to 1 mile, and the reaction time ranges from 0.5 to 10 hours, preferably from about one to 3 hours. The reaction temperatures ranges from 0° to 100° C., preferable from about 30° to 70° C. And, the compound shown by the formula (Ig) can also be produced by allowing the compound shown by the formula (Ie) to react with ethyl chlorocarbonate, followed by subjecting the reaction mixture to reduction in an ether type solvent such as diethyl ether, tetrahydrofuran, dioxane, etc. with sodium borohydride, lithium aluminum hydride, etc. The reaction between the compound shown by the formula (Ie) and ethyl chlorocarbonate can be conducted in an ether type solvent such as ethyl ether, tetrahydrofuran, dioxane, etc., a halogen type solvent such as dichloromethane, chloroform, dichloroethane, etc., or a hydrocarbon type solvent such as hexane, heptane, benzene, toluene, etc., and, when necessary, in the presence of a base (for example, an organic base such as 4-dimethylaminopyridine, triethylamine, triethylenediamine, tetramethylethylenediamine, etc. or, for example, sodium hydrogencarbonate, potassium hydrogencarbonate, sodium carbonate, potassium carbonate, sodium hydride, potassium hydride) etc. Relative to one mole of the compound shown by the formula (Ie), ethyl chlorocarbonate is used usually in an amount ranging from 1 to 5 moles, preferably from about 1 to 2 moles. The reaction temperatures ranges from 0° to 100° C., preferably from 20° to 50° C. The reaction time ranges from 0.5 to 10 hours, preferably from about 1 to 3 hours. In the case of conducting the reduction with sodium borohydride or lithium aluminum hydride, the reducing agent is employed in an amount ranging from 0.1 to 3 moles, preferably from about 0.3 to 1 moles, relative to one mole of the compound obtained by the reaction of ethyl chlorocarbonate. The reaction time ranges from 0.5 to 10 hours, preferably from about 1 to 3 hours, and the reaction temperatures ranges from 0° to 100° C., preferably from about 30° to 70° C.

Among the compounds of the formula (I), a compound represented by the formula (Ih)

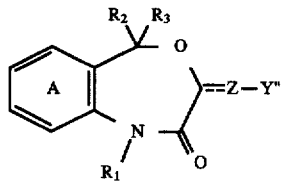

wherein Y" stands for the substituted hydroxyl group defined by Y, and other symbols are of the same meaning as defined above can be produced by allowing the compound shown by the formula (Ig) to react with a compound represented by the formula (VII), W—$R_5$ wherein $R_5$ stands for the substituent of the substituted hydroxyl group defined by Y"; W stands for chlorine, bromine or iodine. More specifically, the compound shown by the formula (Ig) is allowed to react with the compound represented by the formula (VII) in the presence of a base, for example, an inorganic base such as sodium hydrogencarbonate, potassium hydrogencarbonate, sodium carbonate, potassium carbonate, etc., an organic base such as triethylamine, 4-dimethylaminoyridine, triethylenediamine, tetramethyl ethylenediamine, etc., sodium hydride, in a solvent, for example, an alcohol type solvent such as methanol, ethanol, propanol, butanol, etc., an ether type solvent such as diethyl ether, tetrahydrofuran, dioxane, etc., dimethylformamide, etc. Relative to one mole of the compound shown by the formula (Ig), the compound shown by the formula (VII) is used in an amount ranging from 0.5 to 1.5 molar equivalent, and, relative to one mole of the compound shown by the formula (Ig), the base to be used ranges from 1 to 5 molar equivalents, preferably from 1 to 2 molar equivalents. The reaction temperatures ranges from 0° to 200° C., preferably from 20° to 100° C., and the reaction time ranges from 0.5 to 24 hours, preferably from about 1 to 3 hours.

Among the compounds of the formula (I), among the compounds shown by the formula (Ii)

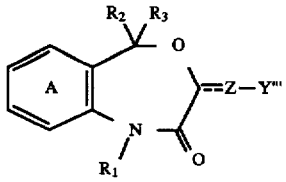

wherein Y'" stands for the optionally substituted amino group defined by Y, and other symbols are of the same meaning as defined above, a compound represented by the formula (Ii')

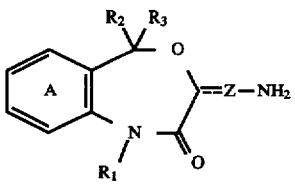

wherein symbols are of the same meaning as defined above can be obtained by, for example, allowing the compound shown by the formula (Ie) to react with diphenylphosphoryl azide in a solvent in the presence of a base. The solvent to be employed in the reaction between the compound shown in the formula (Ie) and diphenylphosphoryl azide may be any one so long as it does not hamper the reaction, which is exemplified by dimethylformamide or a halogen type solvent such as dichloromethane, chloroform, dichloroethane, etc., an ether type solvent such as ethyl ether, tetrahydrofuran, dioxane, etc. As the base to be employed, mention is made of triethylamine, 4-dimethylaminopyridine, triethylenediamine, tetramethylethylenediamine, etc. Relative to 1 mole of the compound shown by the formula (Ie), 1 to 10 molar equivalents, preferably about 1.5 to 3 molar equivalents, of diphenylphosphoryl azide is employed. The reaction temperature ranges from −20° to 50° C., preferably from 0° to 20° C., and the reaction time ranges from 0.5 to 5 hours, preferably from about 1 to 2 hours.

Among the compounds shown by the formula (Ii), the compound represented by the formula (Ii")

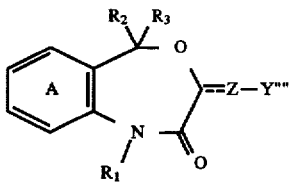

wherein Y"" stands for the substituted amino group defined by Y'", and, other symbols are of the same meaning as defined above can be produced by subjecting the compound shown by the formula (Ii') to diazotization with sodium nitrite, followed by heating (reaction temperatures range from 20° to 200° C., preferably from 50° to 100° C., and the reaction time ranges from 5 minutes to 2 hours, preferably from about 15 to 30 minutes), by allowing an intermediate shown by the formula (VIII)

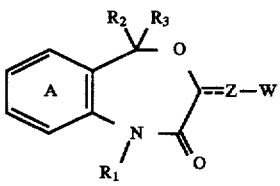

wherein symbols are of the same meaning as defined above, to react with a compound shown by H—Y"" (IX) wherein symbols are of the same meaning as defined above], production was accomplished. The compound shown by the formula (VIII) is allowed to react with a compound shown by the formula (IX) in the presence of a base including an inorganic base such as sodium hydrogencarbonate, potassium hydrogencarbonate, sodium carbonate, potassium carbonate, etc., an organic base such as triethylamine, 4-dimethylaminopyridine, triethylenediamine, tetramethylethylenediamine, etc. or sodium hydride in a solvent, for example, an alcohol type solvent such as methanol, ethanol, propanol, butanol, etc., an ether type solvent such as diethyl ether, tetrahydrofuran, dioxane, etc., dimethylformamide. Relative to one mole of the compound shown by the formula (VIII), the compound shown by the formula (IX) is used in an amount of 0.5 to 1.5 molar equivalents, and, relative to one mole of the compound shown by the formula (VIII), the base to be employed ranges from 1 to 5 molar equivalents, preferably 1 to 2 molar equivalents, and the reaction temperatures ranges from 0° to 200° C., preferably from 20° to 100° C. The reaction time ranges from 0.5 to 24 hours, preferably from about 1 to 3 hours.

Among the compounds of the formula (I), the compound represented by the formula (Ij)

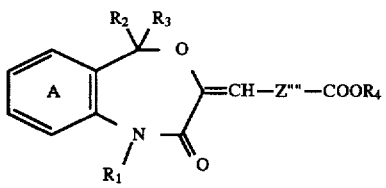

wherein Z'''' stands for a carbon chain optionally containing a double bond, and other symbols are of the same meaning as defined above is converted into chlorine by allowing a compound shown by the formula (Ig')

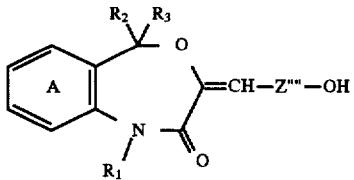

wherein symbols are of the same meaning as defined above to react with thionyl chloride, phosphorus pentachloride, phosphorus oxychloride, etc. in an amount of, relative to one mole of the compound shown by the formula (Ig'), 0.5 to 5 molar equivalents, preferably from 1 to 1.5 molar equivalent, in the absence of a solvent, or in an ether-type solvent such as diethyl ether, tetrahydrofuran, dioxane, etc., a halogen type solvent such as dichloromethane, dichloroethane, chloroform, carbon tetrachloride, etc., at 0° to 200° C., preferably 20° to 50° C., for 0.5 to 5 hours, preferably 1 to 2 hours, then, by allowing thus-obtained intermediate to react with sodium cyanide or potassium cyanide in a solvent such as dimethylformamide, dimethyl sulfoxide, etc, to produce a compound represented by the formula (X)

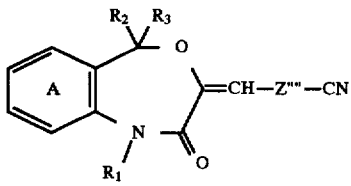

wherein symbols are of the same meaning as defined above. Relative to one mole of the intermediate obtained by converting the hydroxyl group into chlorine, sodium cyanide or potassium cyanide is employed in an amount of 1 to 10 molar equivalents, preferably 1 to 1.5 molar equivalents, and the reaction is allowed to proceed at temperatures ranging from 20° to 200° C., preferably from 50° to 150° C. for 1 to 48 hours, preferably about 5 to 10 hours.

The hydrolysis of thus-obtained compound represented by the formula (X) can be conducted by a per se known method. The hydrolysis can be conducted in the presence of, as a solvent, an alcohol type solvent such as methanol, ethanol, propanol; acid (e.g. hydrogen chloride, sulfuric acid). The reaction temperature ranges from 30° to 150° C., preferably from 50° to 100° C. The reaction time ranges from 10 minutes to 5 hours, preferably from about 30 minutes to one hour.

While the compound (I) of this invention has a squalene synthetase inhibiting action or an antifungal action, among the compounds used in the present invention, there are compounds capable of inhibiting other enzymes in the pathway of cholesterol biosynthesis. Be the matter as it may, the compound (I) of this invention inhibits biosynthesis of cholesterol, which is useful for the prophylaxis or therapy of hypercholesterolemia or coronary sclerosis of mammals (e.g. mouse, rat, rabbit, dog, cat, cow, pig and human being), and also useful for the prophylaxis or therapy of fungal infection.

Also, the compound (I) is useful for therapy of hyperlipidaemia.

The compound (I) of the present invention can be administered to man orally or non-orally. The orally administrable compositions may be in a solid or liquid form, more specifically tablets (including sugar-coated tablets and film-coated tablets), pills, granules, powders, capsules (including soft capsule), syrups, emulsions, suspensions or the like. These compositions can be prepared by a per se known method and contain carriers or excipients conventionally used in the field of pharmaceutical preparation, for example, carriers or excipients such as lactose, starch, sucrose or magnesium stearate for preparing tablets.

The non-orally administrable compositions are exemplified by injections and suppositories, and the injections include hypodermic injections, intradermal injections and intramuscular injections. These injections can be prepared by a per se known method, more specifically, by suspending or emulsifying the compound of this invention in a sterile water or oil conventionally used for preparing injectable compositions. The aqueous liquid to be used for preparation of injections include physiological saline solution and isotonic solution, and, depending on necessity, a suitable suspending agent such as sodium carboxymethyl cellulose, a non-ionic surfactant or the like may be jointly used. As the oil, mention is made of sesame oil, soybean oil, etc., and benzyl benzoate, benzyl alcohol etc. as a solubilizer may be jointly used. Injections thus prepared are, in general, filled in appropriate ampoules.

The compound (I) or salts thereof are low in toxicity and can be used safely. While the daily dosage varies with the conditions or body weight of the subject patient, kinds of the compounds, administration route, etc., in the case of administering the compound of the present invention for the therapy of hypercholesteremia, a daily oral dosage per adult human is about 1 to 500 mg, preferably about 10 to 200 mg. Within this range, no toxicity is observed at all.

Effective daily dose of the compound (I), when administered to mammals (e.g. man) as a squalene synthetase inhibitor, ranges from about 1 to 500 mg, preferably from about 10 to 200 mg in the case of oral administration, while, in the case of non-oral administration (e.g. injection, suppository), ranges from about 0.1 to 100 mg, preferably from about 1 to 20 mg.

Further, the compound (I) shows a broad anti-bacterial activities as determined by the broth or agar dilution method.

Effective daily dose of the compound (I) for the antifungal purpose to be administered to mammals (e.g. man, etc.) ranges from about 0.1 to 100 mg, preferably from about 1 to 50 mg in the case of oral administration, while in the case of non-oral administration (e.g. injection, suppository, etc.) it ranges from about 0.1 to 100 mg, preferably from 1 to 50 mg.

EXAMPLES

The following examples, formulation examples and test examples are intended to illustrate the present invention in further detail and should by no means be construed as defining the metes and bounds of the invention.

In the following description, two types of racemic diastereomers are obtained depending of the kinds of compounds, which is due to the presence of asymmetric carbon atoms at 3- and 5-positions. Isomers in which the substituents at 3- and 5-positions are oriented in the same direction relative to the face of 7-membered ring are named cis-isomers, while those in which the substituents at 3- and 5-positions are oriented in the adverse directions to each other are named trans-isomers. Further, compounds containing asymmetric carbons, for example, (3RS,5RS,αSR) means a mixture of (3R,5R,αS) and (3S,5S,αR).

Example 1

(3RS,5RS,αSR)-7-Chloro-5-(2-chlorophenyl)-1-isopropyl-2-oxo-1,2,3,5-tetrahydro-4,1-benzoxazepine-3-glycolic acid ethyl ester, and (3RS,5SR,αSR)-7-chloro-5-(2-chlorophenyl)-1-isopropyl-2-oxo-1,2,3,5-tetrahydro-4,1-benzoxazepine-3-glycolic acid ethyl ester

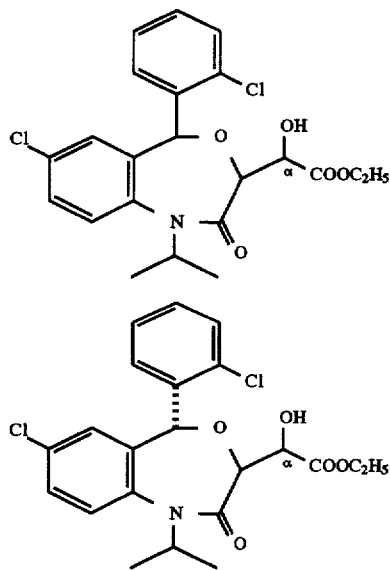

(1) 5-Chloro-α-(2-chlorophenyl)-2-[N-(trans-2,3-epoxy-4-ethoxycarbonyl)butyryl-N-isopropyl]aminobenzylalcohol To a solution of DL-trans-2,3-epoxysuccinic acid monoethyl ester (3.1 g) in methylene chloride (90 ml) was added (dichloromethylene)dimethyliminium chloride (3.14 g) under ice-cooling, and the mixture was stirred for one hour. To the reaction mixture were added 5-chloro-α-(2-chlorophenyl)-2-isopropylaminobenzyl alcohol (4.0 g) and sodium hydrogencarbonate (5.42 g), which was stirred for one hour under ice-cooling. The reaction mixture was washed with water and dried over anhydrous magnesium sulfate, followed by distilling off the solvent under reduced pressure. The residue was purified by means of a silica gel column chromatography (hexane:ethyl acetate=2:1) to give 5-chloro-α-(2-chlorophenyl)-2-[N-(trans-2,3-epoxy-4-ethoxycarbonyl)butyryl-N-isopropyl]aminobenzyl alcohol. (5.6 g) as crystals, m.p. 143°–146° C.

Elemental Analysis for $C_{22}H_{23}Cl_2NO_5$: Calcd.: C, 58.42; H, 5.13; N, 3.10 Found: C, 58.55; H, 5.31; N, 3.12

(2) (3RS,5RS,αSR)-7-Chloro-5-(2-chlorophenyl)-1-isopropyl-2-oxo-1,2,3,5-tetrahydro-4,1-benzoxazepine-3-glycolic acid ethyl ester and (3RS,5SR,αSR)-7-chloro-5-(2-chlorophenyl)-1-isopropyl-2-oxo-1,2,3,5-tetrahydro-4,1-benzoxazepine-3-glycolic acid ethyl ester In ethanol (200 ml) was dissolved 5-chloro-α-(2-chlorophenyl)-2-[N-(trans-2,3-epoxy-4-ethoxycarbonyl)butyryl-N-isopropyl]aminobenzylalcohol (10.0 g). To the solution was added potassium carbonate (3.06 g), which was stirred overnight at room temperature. The solvent was distilled off under reduced pressure. The residue was subjected to extraction by the addition of water (200 ml) and ethyl acetate (300 ml). The ethyl acetate layer was washed with water, which was dried over anhydrous magnesium sulfate, then the solvent was distilled off under reduced pressure. The residue was purified by means of a silica gel column chromatography (hexane:ethyl acetate=2:1) to give 7-chloro-5-(2-chlorophenyl)-1-isopropyl-2-oxo-1,2,3,5-tetrahydro-4,1-benzoxazepine-3-glycolic acid ethyl ester (7.2 g, 72%) as a mixture (1:1) of (3RS,5RS,αSR) compound and (3RS,5SR,αSR) compound. This mixture was recrystallized twice from hexane—ethyl acetate to afford (3RS,5SR,αSR)-7-chloro-5-(2-chlorophenyl)-1-isopropyl-2-oxo-1,2,3,5-tetrahydro-4,1-benzoxazepine-3-glycolic acid ethyl ester (1.75 g) as prisms, m.p. 188°–189° C.

Mass spectrum (m/e): 451 (M⁺)

Elemental Analysis for $C_{22}H_{23}Cl_2NO_5$: Calcd.: C, 58.42; H, 5.13; N, 3.10 Found: C, 58.63; H, 5.31; N, 3.12

Filtrates after the recrystallizations were combined, which was crystallized from hexane—ethyl acetate. Resulting crystals were recrystallized twice from hexane—ethyl acetate to afford (3RS,5RS,αSR)-7-chloro-5-(2-chlorophenyl)-1-isopropyl-2-oxo-1,2,3,5-tetrahydro-4,1-benzoxazepine-3-glycolic acid ethyl ester (1.2 g) as prisms, m.p. 141°–142° C.

Mass spectrum (m/e): 451 (M⁺)

Elemental Analysis for $C_{22}H_{23}Cl_2NO_5$: Calcd.: C, 58.42; H, 5.13; N, 3.10 Found: C, 58.55; H, 5.02; N, 3.11

Example 2

(3RS,5RS,αRS)-7-Chloro-5-(2-chlorophenyl)-1-isopropyl-2-oxo-1,2,3,5-tetrahydro-4,1-benzoxazepine-3-glycolic acid ethyl ester and (3RS,5SR,αRS)-7-chloro-5-(2-chlorophenyl)-1-isopropyl-2-oxo-1,2,3,5-tetrahydro-4,1-benzoxazepine-3-glycolic acid ethyl ester

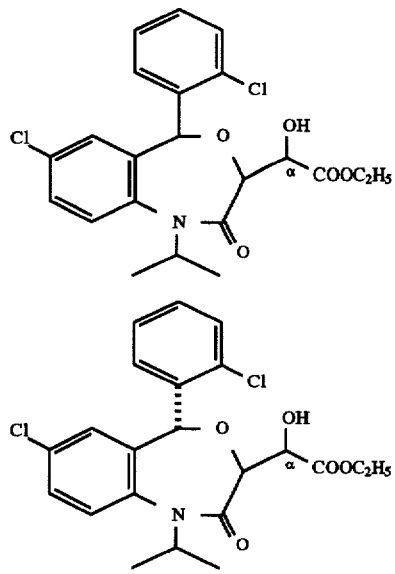

(1) 5-Chloro-α-(2-chlorophenyl)-2-[N-(cis-2,3-epoxy-4-ethoxycarbonyl)butyryl-N-isopropyl]aminobenzylalcohol To a solution of methylene chloride (200 ml) of DL-cis-2,3-epoxy succinic acid monoethyl ester (10.1 g) was added (dichloromethylene)dimethyliminium chloride (10.2 g) under ice-cooling, and the mixture was stirred for one hour. To the reaction mixture were added 5-chloro-α-(2-chlorophenyl)-2-isopropylamimobenzyl alcohol (15.0 g) and sodium hydrogencarbonate (20.3 g), which was stirred for one hour under ice-cooling. The reaction mixture was washed with water, which was dried over anhydrous magnesium sulfate, followed by distilling off the solvent under reduced pressure. The residue was purified by means of a silica gel column chromatography (hexane:ethyl acetate= 2:1) to give 5-chloro-α-(2-chlorophenyl)-2-[N-(cis-2,3-epoxy-4-ethoxycarbonyl)butyryl-N-isopropyl]aminobenzyl alcohol (17.9 g) as crystals, m.p. 139°–141° C.

Elemental Analysis for $C_{22}H_{23}Cl_2NO_5$: Calcd.: C, 58.42; H, 5.13; N, 3.10 Found: C, 58.64; H, 5.13; N, 3.01

(2) (3RS,5RS,αRS)-7-chloro-5-(2-chlorophenyl)-1-isopropyl-2-oxo-1,2,3,5-tetrahydro-4,1-benzoxazepine-3-glycolic acid ethyl ester and (3RS,5SR,αRS)-7-chloro-5-(2-chlorophenyl)-1-isopropyl-2-oxo-1,2,3,5-tetrahydro-4,1-benzoxazepine-3-glycolic acid ethyl ester In ethanol (150 ml) was dissolved 5-chloro-α-(2-chlorophenyl)-2-[N-(cis-2,3-epoxy-4-ethoxycarbonyl)butyryl-N-isopropyl]aminobenzylalcohol (15.0 g). To the solution was added potassium carbonate (4.6 g), which was stirred overnight at room temperature. The solvent was distilled off under reduced pressure. The residue was subjected to extraction by the addition of water (200 ml) and ethyl acetate (300 ml). The ethyl acetate layer was washed with water and dried over anhydrous magnesium sulfate, followed by distilling off the solvent under reduced pressure. The residue was purified by means of a silica gel column chromatography (hexane:ethyl acetate=2:1) to give 7-chloro-5-(2-chlorophenyl)-1-isopropyl-2-oxo-1,2,3,5-tetrahydro-4,1-benzoxazepine-3-glycolic acid ethyl ester (9.0 g, 60%) as a mixture of about 1:1 of (3RS,5RS,αSR) compound and (3RS,5SR,αSR).

IR $v_{max}^{neat}cm^{-1}$: 3440(OH); 1735, 1665(C=O)

Mass spectrum (m/e): 451 (M⁺)

¹H-NMR spectrum (200 MHz,CDCl₃) δ: 1.26(3H,t,J=7.2 Hz), 1.28(3H,d,J=7.2 Hz), 1.55(3H,d,J=7.2 Hz), 4.0–4.1 (1H,m), 4.19(2H,q,J=7.2 Hz), 4.39(1H,d,J=2.8 Hz), 4.50 (1H,dd,J=8.6 Hz,2.8 Hz), 4.7–4.9(1H,m), 5.18(1H,d,J=8.6 Hz), 6.01(1H,s), 6.53(1H,d,J=2.4 Hz), 7.2–7.8(7H,m)

Example 3

7-Chloro-5-(2-chlorophenyl)-1-isobutyl-2-oxo-1,2,3,5-tetrahydro-4,1-benzoxazepine-3-glycolic acid ethyl ester

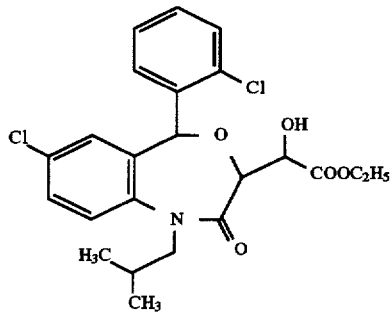

(1) 5-Chloro-α-(2-chlorophenyl)-2-[N-(trans-2,3-epoxy-4-ethoxycarbonyl)butyryl-N-isobutyl] aminobenzyl alcohol Using 5-chloro-α-(2-chlorophenyl)-2-isobutylamino benzylalcohol (10 g), substantially the same procedure as in Example 1-(1) was taken to give an oily compound (14.0 g).

¹H-NMR (CDCl₃) δ: 0.75–1.05(6H,m), 1.15–1.4(3H,m), 1.7–2.0(1H,m), 2.7–3.3(2H,m), 3.3–3.9(2H,m), 4.0–4.45 (3H,m), 6.1–6.4(1H,m), 7.0–7.8(7H,m)

(2) 7-Chloro-5-(2-chlorophenyl)-1-isobutyl-2-oxo-1, 2,3,5-tetrahydro-4,1-benzoxazepine-3-glycolic acid ethyl ester In ethanol (150 ml) were added 5-chloro-α-(2-chlorophenyl)-2-[N-(trans-2,3-epoxy-4-ethoxycarbonyl) butyryl-N-isobutyl]aminobenzyl alcohol (13.0 g) and potassium carbonate (3.85 g). The mixture was stirred overnight at room temperature. The solvent was distilled off. The residue was dissolved in ethyl acetate. The solution was washed with water, which was then dried over anhydrous magnesium sulfate. The solvent was distilled off, and the residue was purified by means of a silica gel column chromatography as colorless crystals (7.0 g).

Elemental Analysis for $C_{23}H_{25}Cl_2NO_5$: Calcd.: C, 59.24; H, 5.40; N, 3.00 Found: C, 59.14; H, 5.37; N, 2.98

¹H-NMR (CDCl₃) δ: 0.7–1.1(6H,m), 1.2–1.4(5H,m), 1.7–2.1(1H,m), 3.35–4.0(2H,m), 4.0–4.8(5H,m), 6.15 and 6.19(1H,each s), 6.55 and 6.96(1H,each d, J=2.4 Hz), 7.15–7.8(6H,m)

Example 4

7-Chloro-5-(2-chlorophenyl)-1-propyl-2-oxo-1,2,3, 5-tetrahydro-4,1-benzoxazepine-3-glycolic acid ethyl ester

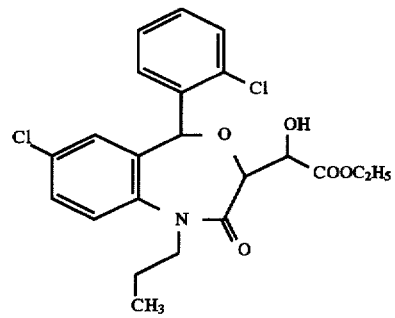

Using 5-chloro-α-(2-chlorophenyl)-2-propylamino benzyl alcohol, production was performed by substantially the same procedures as in Example 1-(1) and Example 3-(2).

(1) 5-Chloro-α-(2-chlorophenyl)-2-[N-(trans-2,3-epoxy-4-ethoxycarbonyl)butyryl-N-propyl] aminobenzyl alcohol an oily compound ¹H-NMR(CDCl₃) δ: 0.75–1.05(3H,m), 1.1–1.8(5H,m), 2.6–3.9(4H,m), 4.0–4.5(3H,m), 6.1–6.4(1H,m), 6.9–7.9(7H, m)

(2) 7-Chloro-5-(2-chlorophenyl)-1-propyl-2-oxo-1,2, 3,5-tetrahydro-4,1-benzoxazepine-3-glycolic acid ethyl ester Colorless crystals Elemental Analysis for $C_{22}H_{23}Cl_2NO_5$: Calcd.: C, 58.42; H, 5.12; N, 3.10 Found: C, 58.40; H, 5.23; N, 3.01

¹H-NMR (CDCl₃) δ: 0.7–1.05(3H,m), 1.15–1.4(3H,m), 1.45–1.8(2H,m), 3.4–3.9(2H,m), 4.0–4.7(4H,m), 6.08 and 6.10(1H,each s), 6.5–7.8(7H,m)

Example 5

(3RS,5SR,αSR)-7-Chloro-5-(2-chlorophenyl)-1-isopropyl-2-oxo-1,2,3,5-tetrahydro-4,1-benzoxazepine-3-glycolic acid

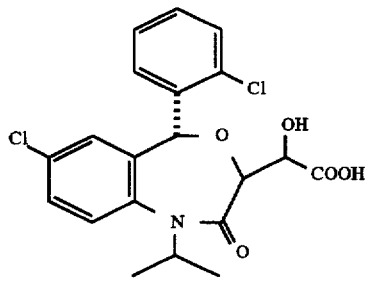

In ethanol (8 ml) was dissolved (3RS,5SR,αSR)-7-chloro-5-(2-chlorophenyl)-1-isopropyl-2-oxo-1,2,3,5-tetrahydro-4,1-benzoxazepine-3-glycolic acid ethyl ester (0.3 g) obtained in Example 1. To the solution was added 1N sodium hydroxide (2 ml), and the mixture was left standing for 20 minutes at room temperature. To the resultant mixture was added 1N hydrochloric acid (50 ml) to make the solution acid, followed by extraction with ethyl acetate (50 ml). The extract solution was washed with water, dried over anhydrous magnesium sulfate, then the solvent was distilled off under reduced pressure to give (3RS,5SR,αSR)-7-chloro-5-(2-chlorophenyl)-1-isopropyl-2-oxo-1,2,3,5-tetrahydro-4,1-benzoxazepine-3-glycolic acid (0.26 g) as prisms, m.p. 245°–247° C. (decomp.).

Elemental Analysis for $C_{20}H_{19}Cl_2NO_5$: Calcd.: C, 56.62; H, 4.51; N, 3.30 Found: C, 56.47; H, 4.40; N, 3.32

Example 6

(3RS,5RS,αSR)-7-Chloro-5-(2-chlorophenyl)-1-isopropyl-2-oxo-1,2,3,5-tetrahydro-4,1-benzoxazepine-3-glycolic acid

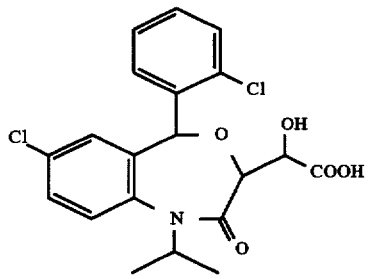

(3RS,5RS,αSR)-7-Chloro-5-(2-chlorophenyl-1-isopropyl-2-oxo-1,2,3,5-tetrahydro-4,1-benzoxazepine-3-glycolic acid ethyl ester (0.3 g) obtained in Example 1 was subjected to substantially the same procedure as in Example 5 to afford 0.26 g of colorless crystals, m.p. 237°–239° C. (decomp.).

Elemental Analysis for $C_{20}H_{19}Cl_2NO_5$: Calcd.: C, 56.62; H, 4.51; N, 3.30 Found: C, 56.83; H, 4.62; N, 3.34

Example 7

(3RS,5RS,αRS)-7-Chloro-5-(2-chlorophenyl)-1-isopropyl-2-oxo-1,2,3,5-tetrahydro-4,1-benzoxazepine-3-glycolic acid and, (3RS,5SR,αRS)-7-Chloro-5-(2-chlorophenyl)-1-isopropyl-2-oxo-1,2,3,5-tetrahydro-4,1-benzoxazepine-3-glycolic acid

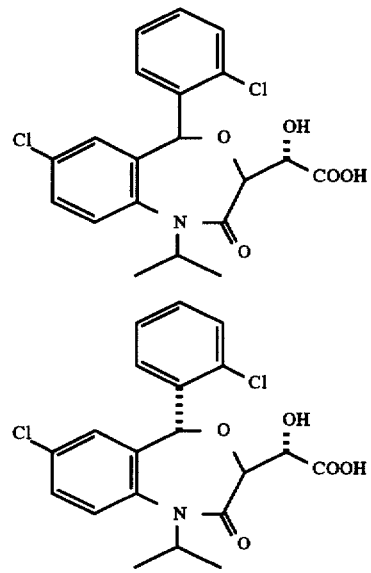

A mixture (4.5 g) of (3RS,5RS,αRS)-7-chloro-5-(2-chlorophenyl)-1-isopropyl-2-oxo-1,2,3,5-tetrahydro-4,1-benzoxazepine-3-glycolic acid ethyl ester and (3RS,5SR,αRS)-7-chloro-5-(2-chlorophenyl)-1-isopropyl-2-oxo-1,2,3,5-tetrahydro-4,1-benzoxazepine-3-glycolic acid ethyl ester obtained in Example 2 was dissolved in ethanol (50 ml). To the solution was added 1N sodium hydroxide (30 ml), and mixture was stirred for 30 minutes at room temperature. To the resultant mixture was added 1N hydrochloric acid (100 ml) to make the solution acid, which was extracted with ethyl acetate (200 ml). The extract solution was washed with water, dried over anhydrous magnesium sulfate, then the solvent was distilled off under reduced pressure. The residue was crystallized from hexane-ethyl acetate to give a mixture (3.3 g) of (3RS,5RS,αRS)-7-chloro-5-(2-chlorophenyl)-1-isopropyl-2-oxo-1,2,3,5-tetrahydro-4,1-benzoxazepine-3-glycolic acid and (3RS,5SR,αRS)-7-chloro-5-(2-chlorophenyl)-1-isopropyl-2-oxo-1,2,3,5-tetrahydro-4,1-benzoxazepine-3-glycolic acid. This mixture was recrystallized twice from hexane-ethanol to give (3RS,5SR,αRS)-7-chloro-5-(2-chlorophenyl)-1-isopropyl-2-oxo-1,2,3,5-tetrahydro-4,1-benzoxazepine-3-glycolic acid (0.94 g) as plates, m.p. 226°–230° C. (decomp.).

Elemental Analysis for $C_{20}H_{19}Cl_2NO_5 \cdot EtOH$: Calcd.: C, 56.18; H, 5.36; N, 2.98 Found: C, 56.12; H, 5.41; N, 2.96

Filtrates after recrystallizations were combined, which was subjected to distillation under reduced pressure to leave crystals, which were recrystallized twice from hexane-ethanol to give (3RS,5RS,αRS)-7-chloro-5-(2-chlorophenyl)-1-isopropyl-2-oxo-1,2,3,5-tetrahydro-4,1-benzoxazepine-3-glycolic acid (0.49 g) as plates, m.p. 220°–224° C. (decomp.).

Elemental Analysis for $C_{20}H_{19}Cl_2NO_5$: Calcd.: C, 56.62; H, 4.51; N, 3.30 Found: C, 56.80; H, 4.80; N, 3.24

Example 8

(3RS,5SR,αRS)-7-chloro-5-(2-chlorophenyl)-1-isopropyl-2-oxo-1,2,3,5-tetrahydro-4,1-benzoxazepine-3-glycolic acid ethyl ester

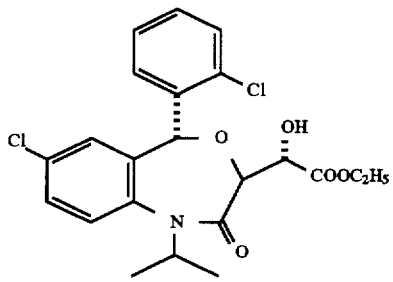

A mixture of (3RS,5SR,αRS)-7-chloro-5-(2-chlorophenyl)-1-isopropyl-2-oxo-1,2,3,5-tetrahydro-4,1-benzoxazepine-3-glycolic acid (0.15 g) obtained in Example 7, p-toluenesulfonic acid monohydrate (6 mg) and ethanol (20 ml) was heated for 10 hours under reflux. Ethanol was distilled off under reduced pressure. To the residue were added water (50 ml) and ethyl acetate (50 ml). The organic layer was washed with an aqueous solution of sodium hydrogencarbonate, dried over anhydrous magnesium sulfate, followed by distilling off the solvent under reduced pressure to leave (3RS,5SR,αRS)-7-chloro-5-(2-chlorophenyl)-1-isopropyl-2-oxo-1,2,3,5-tetrahydro-4,1-benzoxazepine-3-glycolic acid ethyl ester (95 mg) as prisms, m.p. 126°–128° C.

Elemental Analysis for $C_{22}H_{23}Cl_2NO_5$: Calcd.: C, 58.42; H, 5.13; N, 3.10 Found: C, 58.31; H, 5.15; N, 3.15

Example 9

(3RS,5RS,αRS)-7-Chloro-5-(2-chlorophenyl)-1-isopropyl-2-oxo-1,2,3,5-tetrahydro-4,1-benzoxazepine-3-glycolic acid ethyl ester

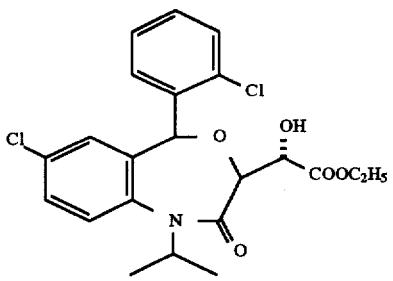

A mixture of (3RS,5RS,αRS)-7-chloro-5-(2-chlorophenyl)-1-isopropyl-2-oxo-1,2,3,5-tetrahydro-4,1-benzoxazepine-3-glycolic acid (0.15 g) obtained in Example 7, p-toluenesulfonic acid monohydrate (7 mg) and ethanol (20 ml) was heated for 24 hours under reflux. Ethanol was distilled off under reduced pressure. The residue was dissolved in a mixture of water (50 ml) and ethyl acetate (50 ml). The organic layer was washed with an aqueous solution of sodium hydrogencarbonate, which was dried over anhydrous magnesium sulfate, then the solvent was was distilled off under reduced pressure to leave (3RS,5RS,αRS)-7-chloro-5-(2-chlorophenyl)-1-isopropyl-2-oxo-1,2,3,5-tetrahydro-4,1-benzoxazepine-3-glycolic acid ethyl ester (0.14 g) as prisms, m.p. 119°–120° C.

Elemental Analysis for $C_{22}H_{23}Cl_2NO_5$: Calcd.: C, 58.42; H, 5.13; N, 3.10 Found: C, 58.53; H, 5.18; N, 3.26

Example 10

(Z)-7-Chloro-5-(2-chlorophenyl)-1-isopropyl-2-oxo-1,2,3,5-tetrahydro-4,1-benzoxazepine-3-Δ(3,α)-acetic acid ethyl ester and, (E)-7-chloro-5-(2-chlorophenyl)-1-isopropyl-2-oxo-1,2,3,5-tetrahydro-4,1-benzoxazepine-3-Δ(3,α)-acetic acid ethyl ester

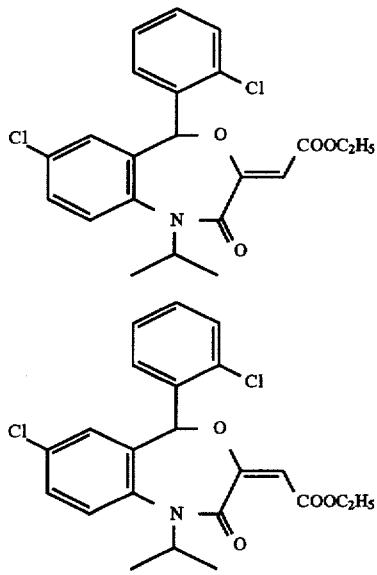

(1) (3RS,5SR,αSR)-7-chloro-5-(2-chlorophenyl)-1-isopropyl-2-oxo-4,1-benzoxazepine-3-α-(methanesulfonyloxy)acetic acid ethyl ester In ethyl acetate (30 ml) was dissolved (3RS,5SR,αSR)-7-chloro-5-(2-chlorophenyl)-1-isopropyl-2-oxo-4,1-benzoxazepine-3-glycolic acid ethyl ester (0.8 g) obtained in Example 1. To the solution were added methanesulfonyl chloride (0.18 ml) and triethylamine (0.32 ml) under ice-cooling, and the mixture was stirred for one hour at room temperature. The reaction mixture was washed with water, dried over anhydrous magnesium sulfate, then the solvent was distilled off under reduced pressure. The residue was purified by means of a silica gel column chromatography (hexane:methylene chloride:ethyl acetate=10:5:1) to afford (3RS,5SR,αSR)-7-chloro-5-(2-chlorophenyl)-1-isopropyl-2-oxo-4,1-benzoxazepine-3-α-(methanesulfonyloxy)acetic acid ethyl ester (0.82 g) as prisms, m.p. 159°–160° C.

Elemental Analysis for $C_{23}H_{25}Cl_2NO_7S$; Calcd.: C, 52.08; H, 4.75; N, 2.64 Found: C, 52.25; H, 4.80; N, 2.74

(2) (Z)-7-Chloro-5-(2-chlorophenyl)-1-isopropyl-2-oxo-1,2,3,5-tetrahydro-4,1-benzoxazepine-3-Δ(3,α)-acetic acid ethyl ester and, (E)-7-chloro-5-(2-chlorophenyl)-1-isopropyl-2-oxo-1,2,3,5-tetrahydro-4,1-benzoxazepine-3-Δ(3,α)-acetic acid ethyl ester In methanol (10 ml) was dissolved propionic acid (0.23 g), to which was added cesium carbonate (0.34 g), and the mixture was stirred for 30 minutes at room temperature. Methanol was distilled off under reduced pressure. To the residue was added toluene (10 ml), which was again subjected to distillation under reduced pressure to leave cesium propionate as a powdery product. A mixture of this product, (3RS,5SR,αSR)-7-chloro-5-(2-chlorophenyl)-1-isopropyl-2-oxo-4,1-benzoxazepine-3-α-(methanesulfonyloxy) acetic acid ethyl ester (1.0 g) and N,N-dimethylformamide (10 ml) was stirred for 2 hours at 80° C. After adding water (50 ml), the mixture was extracted with ethyl acetate (100 ml). The ethyl acetate layer was washed with 1N hydrochloric acid and an aqueous solution of sodium hydrogencarbonate, which was then dried over anhydrous magnesium sulfate, and the solvent was distilled off under reduced pressure. The residue was purified by means of a silica gel column chromatography (hexane:ethyl acetate=10:1–5:1). From the first fraction, (Z)-7-chloro-5-(2-chlorophenyl)-1-isopropyl-2-oxo-1,2,3,5-tetrahydro-4,1-benzoxazepine-3-Δ(3,α)-acetic acid ethyl ester (0.31 g) as prisms, m.p. 194°–195° C.

Mass spectrum (m/e): 433 (M+)

Elemental Analysis for $C_{22}H_{21}Cl_2NO_4$: Calcd.: C, 60.84; H, 4.87; N, 3.22 Found: C, 60.76; H, 4.99; N, 3.32

And, from the second fraction, (E)-7-chloro-5-(2-chlorophenyl)-1-isopropyl-2-oxo-1,2,3,5-tetrahydro-4,1-benzoxazepine-3-Δ(3,α)-acetic acid ethyl ester (0.13 g) was obtained as prisms, m.p. 143°–144° C.

Mass spectrum (m/e): 433 (M+)

Elemental Analysis for $C_{22}H_{21}Cl_2NO_4$: Calcd.: C, 60.84; H, 4.87; N, 3.22 Found: C, 60.59; H, 4.84; N, 3.30

In like manner, (3RS,5RS,αSR)-7-chloro-5-(2-chlorophenyl)-1-isopropyl-2-oxo-4,1-benzoxazepine-3-α-(methanesulfonyloxy)acetic acid ethyl ester (1.0 g) was allowed to react with cesium propionate, followed by purification by means of a silica gel column chromatography. From the first fraction, (Z)-7-chloro-5-(2-chlorophenyl)-1-isopropyl-2-oxo-1,2,3,5-tetrahydro-4,1-benzoxazepine-3-Δ(3,α)-acetic acid ethyl ester (0.335 g) was obtained as prisms. And, from the second fraction, was obtained (E)-7-chloro-5-(2-chlorophenyl)-1-isopropyl-2-oxo-1,2,3,5-tetrahydro-4,1-benzoxazepine-3-Δ(3,α)-acetic acid ethyl ester (0.17 g) as prisms.

(3) (3RS,5RS,αSR)-7-chloro-5-(2-chlorophenyl)-1-isopropyl-2-oxo-4,1-benzoxazepine-3-α-(methanesulfonyloxy)acetic acid ethyl ester In ethyl acetate (30 ml) was dissolved (3RS,5RS,αSR)-7-chloro-5-(2-chlorophenyl)-1-isopropyl-2-oxo-4,1-benzoxazepine-3-glycolic acid ethyl ester (0.6 g). To the solution were added methanesulfonyl chloride (0.13 ml) and triethylamine (0.24 ml) under ice-cooling. The mixture was stirred for one hour at room temperature. The reaction mixture was washed with water, dried over anhydrous magnesium sulfate, followed by distilling off the solvent under reduced pressure. The residue was purified by means of a silica gel column chromatography (hexane: methylene chloride: ethyl acetate=10:5:1) to give (3RS,5RS,αSR)-7-chloro-5-(2-chlorophenyl)-1-isopropyl-2-oxo-4,1-benzoxazepine-3-α-(methanesulfonyloxy)acetic acid ethyl ester (0.63 g) as prisms, m.p. 143°–144° C.

Elemental Analysis for $C_{23}H_{25}Cl_2NO_7S$: Calcd.: C, 52.08; H, 4.75; N, 2.64 Found: C, 52.38; H, 4.89; N, 2.77

Example 11

(Z)-7-Chloro-5-(2-chlorophenyl)-1-isopropyl-2-oxo-1,2,3,5-tetrahydro-4,1-benzoxazepine-3-Δ(3,α)-acetic acid

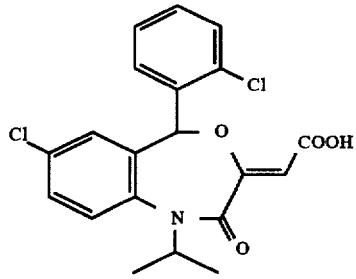

To the solution of (2-chlorophenyl)-1-isopropyl-2-oxo-1,2,3,5-tetrahydro-4,1-benzoxazepine-3-Δ(3,α)-acetic acid ethyl ester (0.3 g) obtained in example 10 in methanol (30 ml) was added an aqueous solution of sodium hydroxide (5 ml). The solution was stirred for one hour at 50° C. Methanol was distilled off under reduced pressure. To the residue were added 1N hydrochloric acid (50 ml) and ethyl acetate (100 ml). The ethyl acetate layer was washed with water and dried over anhydrous magnesium sulfate. The solvent was distilled off under reduced pressure to leave (Z)-7-chloro-5-(2-chlorophenyl)-1-isopropyl-3-oxo-1,2,3,5-tetrahydro-4,1-benzoxazepine-3-Δ(3,α)acetic acid (0.26 g) as prisms, m.p. 234°–239° C.

IR $v_{max}^{KBr}$cm$^{-1}$: 1670, 1655 (C=O, C=C)

Elemental Analysis for $C_{20}H_{17}Cl_2NO_4$: Calcd.: C, 59.13; H, 4.22; N, 3.45 Found: C, 59.02; H, 4.21; N, 3.37

$^1$H-NMR spectrum (200 MHz,CDCl$_3$) δ: 1.31(3H,d,J=7.0 Hz), 1.61(3H,d,J=7.0 Hz), 4.7–4.9(1H,m), 5.48(1H,s), 6.54 (1H,s), 6.57(1H,d,J=2.2 Hz), 7.3–7.6(5H,m), 8.05(1H,d,J=7.8 Hz)

Example 12

(E)-7-Chloro-5-(2-chlorophenyl)-1-isopropyl-2-oxo-1,2,3,5-tetrahydro-4,1-benzoxazepine-3-Δ(3α)-acetic acid

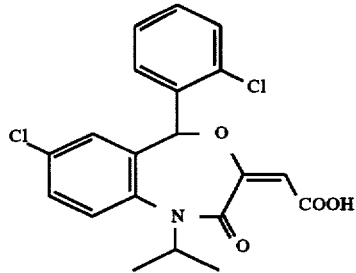

In methanol (20 ml) was dissolved (E)-7-chloro-5-(2-chlorophenyl)-1-isopropyl-2-oxo-1,2,3,5-tetrahydro-4,1-benzoxazepine-3-Δ(3,α)-acetic acid ethyl ester (0.16 g) obtained in Example 10. To the solution was added an aqueous solution of sodium hydroxide (5 ml). The mixture was stirred for one hour at 50° C. Methanol was distilled off under reduced pressure. The residue was subjected to extraction by the addition of 1N hydrochloric acid (50 ml) and ethyl acetate (100 ml). The ethyl acetate layer was washed with water, dried over anhydrous magnesium sulfate. The solvent was distilled off under reduced pressure to leave (E)-7-chloro-5-(2-chlorophenyl)-1-isopropyl-2-oxo-1,2,3,5-tetrahydro-4,1-benzoxazepine-3-Δ(3,α)-acetic acid (0.135 g) as prisms, m.p. 209°–214° C.

IR $\nu_{max}^{KBr}$cm$^{-1}$: 1720, 1650, 1630 (C=O,C=C)

Elemental Analysis for $C_{20}H_{17}Cl_2NO_4$: Calcd.: C, 59.13; H, 4.22; N, 3.45 Found: C, 58.97; H, 4.24; N, 3.42

$^1$H-NMR spectrum (200 MHz,CDCl$_3$) δ: 1.34(3H,d,J=7.0 Hz), 1.62(3H,d,J=7.0 Hz), 4.8–5.0(1H,m), 5.41(1H,s), 6.51 (1H,s), 6.54(1H,d,J=1.8 Hz), 7.3–7.6(5H,m), 7.78(1H,d,J= 7.0 Hz)

Example 13

By substantially the same procedures as in Example 10, Example 12 and Example 13, compounds listed in [Table 1] were obtained.

TABLE 1

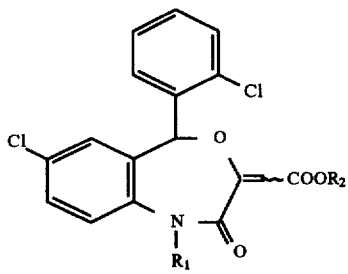

| Compd. No. | R$_1$ | R$_2$ | = bond steric | m.p. (°C.) | Molecular Formula | Elemental Analysis (Found) C | H | N |
|---|---|---|---|---|---|---|---|---|
| 1 | CH$_2$CH$_2$CH$_3$ | C$_2$H$_5$ | Z | 171–172 | C$_{22}$H$_{21}$Cl$_2$NO$_4$ | 60.84 (60.65 | 4.87 4.73 | 3.22 3.15) |
| 2 | CH$_2$CH$_2$CH$_3$ | C$_2$H$_6$ | E | 114–115 | C$_{22}$H$_{21}$Cl$_2$NO$_4$ | 60.84 (60.85 | 4.87 5.17 | 3.22 3.13) |
| 3 | CH$_2$CH$_2$CH$_3$ | H | Z | 208–210 (decomp) | C$_{20}$H$_{17}$Cl$_2$NO$_4$ | 59.13 (59.20 | 4.22 4.39 | 3.45 3.32) |
| 4 | CH$_2$CH$_2$CH$_3$ | H | E | 192–194 (decomp.) | C$_{20}$H$_{17}$Cl$_2$NO$_4$ | 59.13 (58.88 | 4.22 4.34 | 3.45 3.27) |
| 5 | CH$_2$CH(CH$_3$)$_2$ | C$_2$H$_5$ | Z | 181–182 | C$_{23}$H$_{23}$Cl$_2$NO$_4$ | 61.62 (61.54 | 5.17 5.30 | 3.12 3.09) |
| 6 | CH$_2$CH(CH$_3$)$_2$ | C$_2$H$_5$ | E | oily | C$_{23}$H$_{23}$Cl$_2$NO$_4$ | (a) | | |
| 7 | CH$_2$CH(CH$_3$)$_2$ | H | Z | 236–238 (decomp.) | C$_{21}$H$_{19}$Cl$_2$NO$_4$ | 60.01 (60.16 | 4.56 4.56 | 3.33 3.50) |
| 8 | CH$_2$CH(CH$_3$)$_2$ | H | E | 207–209 (decomp.) | C$_{21}$H$_{19}$Cl$_2$NO$_4$ | 60.01 (59.95 | 4.56 4.65 | 3.33 3.45) |

(a)$^1$H-NMR(CDCl$_3$)δ: 0.95(3H, d, J=6.6Hz), 1.07(3H, d, J=6.6Hz), 1.9–2.2(1H, m), 3.57(1H, dd, J=14.0, 5.8Hz), 4.0–4.25(2H, m), 4.37(1H, dd, J=14.0, 8.6Hz), 5.44(1H, s), 6.54(1H, d, J=1.8Hz), 6.57(1H, s), 7.3–7.9(6H, m)

Example 14

(3RS,5SR,αRS)-7-Chloro-5-(2-chlorophenyl)-2-oxo-1-propyl-1,2,3,5-tetrahydro-4,1-benzoxazepine-3-(α-hydroxy)propionic acid ethyl ester and (3RS,5SR,αSR)-7-chloro-5-(2-chlorophenyl)-2-oxo-1-propyl-1,2,3,5-tetrahydro-4,1-benzoxazepine-3-(α-hydroxy)propionic acid ethyl ester

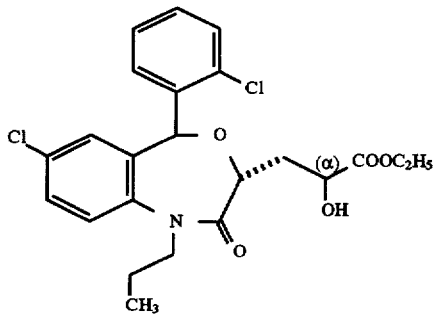

(1) 3,5-trans-7-Chloro-5-(2-chlorophenyl)-2-oxo-1-propyl-1,2,3,5-tetrahydro-4,1-benzoxazepine-3-ethanol To a solution of tetrahydrofuran (30 ml) of 3,5-trans-7-chloro-5-(2-chlorophenyl)-2-oxo-1-propyl-1,2,3,5-tetrahydro-4,1-benzoxazepine-3-acetic acid (3.0 g) and N-methylmorpholine (0.97 ml) was added ethyl chloroformate (0.84 ml) at −10° C. The mixture was stirred for 10 minutes. To the reaction mixture was added sodium borohydride (0.93 g), and the mixture was stirred for 10 minutes at room temperature. The solvent was distilled off, and the residue was made acid with dilute hydrochloric acid, which was extracted with ethyl acetate. The extract solution was dried over anhydrous magnesium sulfate. The solvent was distilled off. The residue was purified by means of a silica gel column chromatography to afford colorless crystals (2.27 g), m.p. 184°–186° C.

Elemental Analysis for $C_{20}H_{21}Cl_2NO_3$: Calcd.: C, 60.92; H, 5.37; N, 3.55 Found: C, 61.03; H, 5.27; N, 3.53

(2) 3,5-trans-7-Chloro-5-(2-chlorophenyl)-2-oxo-1-propyl-1,2,3,5-tetrahydro-4,1-benzoxazepine-3-acetaldehyde To a solution of oxalyl chloride (0.60 ml) in dichloromethane (5 ml) was added a solution of dimethylsulfoxide (0.53 ml) in dichloromethane (2 ml) dropwise at −65° C., taking 5 minutes. The mixture was stirred for 5 minutes. To the reaction mixture was added dropwise a solution of the compound (2.1 g) obtained in (1), then, the mixture was stirred for 15 minutes at −65° C. To the mixture was added triethylamine (2.9 ml) at the same temperature, then the mixture was stirred for 10 minutes at room temperature. To the reaction mixture was added 1N hydrochloric acid (50 ml). The organic layer was dried over anhydrous magnesium sulfate. The solvent was distilled off. The residue was recrystallized from hexane/dichloromethane to give 1.64 g of colorless crystals, m.p. 157°–159° C.

Elemental Analysis for $C_{20}H_{19}Cl_2NO_3 \cdot 0.4H_2O$: Calcd.: C, 60.13; H, 5.00; N, 3.51 Found: C, 60.24; H, 4.86; N, 3.57

(3) (3RS,5SR,αRS)-7-chloro-5-(2-chlorophenyl)-2-oxo-1-propyl-1,2,3,5-tetrahydro-4,1-benzoxazepine-3-acetaldehyde cyanohydrin, (3RS,5SR,αSR)-7-chloro-5-(2-chlorophenyl)-2-oxo-1-propyl-1,2,3,5-tetrahydro-4,1-benzoxazepine-3-acetaldehyde cyanohydrine A mixture of the compound (1.5 g) obtained in (2), acetone cyanohydrin (5 ml) and triethylamine (0.1 ml) was stirred for 30 minutes at room temperature. To the reaction mixture was added ethyl ether, which was washed with water and dried over anhydrous magnesium sulfate. The solvent was distilled off, and the residue was purified by means of a silica gel column chromatography. From the first fraction, (3RS,5SR,αRS) derivative was obtained as colorless crystals (0.42 g), m.p. 159°–162° C.

Elemental Analysis for $C_{21}H_{20}Cl_2N_2O_3$: Calcd.: C, 60.15; H, 4.81; N, 6.68 Found: C, 60.18; H, 4.97; N, 6.54

From the second fraction, (3RS,5SR,αSR) derivative was obtained as colorless crystals (0.61 g), m.p. 177°–180° C.

Elemental Analysis for $C_{21}H_{20}Cl_2N_2O_3$: Calcd.: C, 60.15; H, 4.81; N, 6.68 Found: C, 59.94; H, 4.76; N, 6.52

(4) (3RS,5SR,αRS)-7-Chloro-5-(2-chlorophenyl)-2-oxo-1-propyl-1,2,3,5-tetrahydro-4,1-benzoxazepine-3-(α-hydroxy)propionic acid ethyl ester In a mixture solvent consisting of ethanol (10 ml) and dioxane solution of 4N hydrogen chloride (10 ml) was dissolved the (3RS,5SR,αRS) derivative (0.40 g) obtained in (3). The solution was stirred for 30 minutes under heating. The solvent was distilled off, and the residue was dissolved in acetic acid ethyl ester. The solution was washed with a saturated aqueous solution of sodium hydrogencarbonate, which was dried over anhydrous magnesium sulfate. The solvent was distilled off, and the residue was purified by means of a silica gel column chromatography to give 0.40 g of an oily compound.

$^1$H-NMR(CDCl$_3$) δ: 0.97(3H,t,J=7.4 Hz), 1.27(3H,t,7,2 Hz), 1.5–1.9(1H,d,J=6.2 Hz), 3.4–3.6(1H,m), 4.0–4.5(4H, m), 6.08(1H,s), 6.52(1H,d,J=2.4 Hz), 7.2–7.8(6H,m) (5) (3RS,5SR,αSR)-7-Chloro-5-(2-chlorophenyl)-2-oxo-1-propyl-1,2,3,5-tetrahydro-4,1-benzoxazepine-3-(α-hydroxy)propionic acid ethyl ester From the (3RS,5SR,αSR) derivative obtained in (3) (0.45 g), an oily compound (0.45 g) was obtained by substantially the same procedure as in (4).

$^1$H-NMR(CDCl$_3$) δ: 0.97(3H,t,J=7.4 Hz), 1.18(3H,t,J=7.1 Hz), 1.5–1.9(2H,m), 2.3–2.5(2H,m), 3.18(1H,d,J=4.6 Hz), 3.4–3.6(1H,m), 4.0–4.5(4H,m), 6.03(1H,s), 6.50(1H,d,J=2.4 Hz), 7.2–7.8(6H,m)

Example 15

(3RS,5SR,αRS)-7-Chloro-5-(2-chlorophenyl)-2-oxo-1-propyl-1,2,3,5-tetrahydro-4,1-benzoxazepine-3-(α-hydroxy)propionic acid

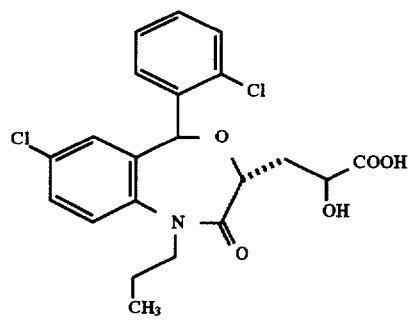

In ethanol (3 ml) was dissolved the compound (0.2 g) obtained in Example 14-(4). To the solution was added 1N aqueous solution of sodium hydroxide (1 ml), and the mixture was stirred for 15 minutes at room temperature. To the reaction mixture was added 1N hydrochloric acid (50 ml), and the mixture was extracted with acetic acid ethyl ester. The extract was washed with water and dried over anhydrous magnesium sulfate. The solvent was distilled off, and the residue was recrystallized from hexane to give colorless crystals (0.15 g), m.p. 210°–214° C.

Elemental Analysis for $C_{21}H_{21}Cl_2NO_5$: Calcd.: C, 57.55; H, 4.83; N, 3.20 Found: C, 57.38; H, 4.93; N, 2.90

Example 16
(3RS,5SR,αSR)-7-Chloro-5-(2-chlorophenyl)-2-oxo-1-propyl-1,2,3,5-tetrahydro-4,1-benzoxazepine-3-(α-hydroxy)propionic acid

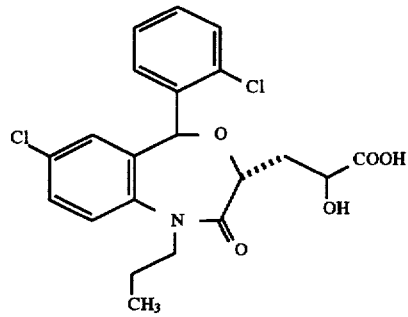

From the compound (0.2 g) obtained in-Example 14-(5), 0.16 g of a colorless crystalline product was obtained by substantially the same procedure as in Example 15, m.p. 138°–141° C.

Elemental Analysis for $C_{21}H_{21}Cl_2NO_5$: Calcd.: C, 57.55; H, 4.83; N, 3.20 Found: C, 57.27; H, 5.03; N, 2.95

Example 17
By substantially the same procedures as in Example 14 and Example 15, compounds set forth in [Table 2] and [Table 3] were obtained.

TABLE 2

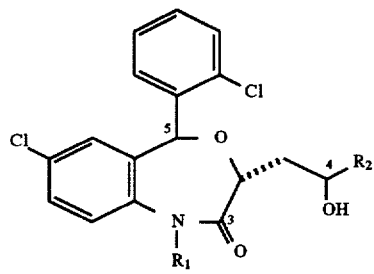

| Compd. No. | $R_1$ | $R_2$ | Steric Configuration | m.p. (°C.) | Molecular Formula | Elemental Analysis (Found) C | H | N |
|---|---|---|---|---|---|---|---|---|
| inter-mediate | $CH(CH_3)_2$ | CN | (3RS, 5SR, αRS) | 142–145 | $C_{21}H_{20}Cl_2N_2O_3$ | 60.15 (60.16 | 4.81 4.96 | 6.68 6.63) |
| inter-mediate | $CH(CH_3)_2$ | CN | (3RS, 5SR, αSR) | 181–184 | $C_{21}H_{20}Cl_2N_2O_3$ | 60.15 (59.97 | 4.81 4.90 | 6.68 6.64) |
| inter-mediate | $CH_2CH(CH_3)_2$ | CN | (3RS, 5SR, αRS) | 169–172 | $C_{22}H_{22}Cl_2N_2O_3$ | 60.98 (61.06 | 5.12 5.10 | 6.46 6.38) |
| inter-mediate | $CH_2CH(CH_3)_2$ | CN | (3RS, 5SR, αSR) | 178–181 | $C_{22}H_{22}Cl_2N_2O_3$ | 60.98 (61.15 | 5.12 5.01 | 6.46 6.52) |
| 1 | $CH(CH_3)_2$ | $COOC_2H_5$ | (3RS, 5SR, αRS) | oily | | a | | |
| 2 | $CH(CH_3)_2$ | $COOC_2H_5$ | (3RS, 5SR, αSR) | oily | | b | | |
| 3 | $CH_2CH(CH_3)_2$ | $COOC_2H_5$ | (3RS, 5SR, αRS) | oily | | c | | |
| 4 | $CH_2CH(CH_3)_2$ | $COOC_2H_5$ | (3RS, 5SR, αSR) | oily | | d | | |
| 5 | $CH(CH_3)_2$ | COOH | (3RS, 5SR, αRS) | 197–201 | $C_{21}H_{21}Cl_2NO_5$ | 57.55 (57.61 | 4.83 5.03 | 3.20 3.13) |

TABLE 3

| Compd. No. | R₁ | R₂ | Steric Configuration | m.p. (°C.) | Molecular Formula | Elemental Analysis (Found) C | H | N |
|---|---|---|---|---|---|---|---|---|
| 6 | CH(CH₃)₂ | COOH | (3RS, 5SR, αSR) | 204–208 | C₂₁H₂₁Cl₂NO₅ | 57.55 (57.63 | 4.83 4.96 | 3.20 3.36) |
| 7 | CH₂CH(CH₃)₂ | COOH | (3RS, 5SR, αRS) | 209–211 | C₂₂H₂₃Cl₂NO₅·0.2C₆H₁₄ | 59.34 (59.38 | 5.54 5.67 | 2.98 3.09) |
| 8 | CH₂CH(CH₃)₂ | COOH | (3RS, 5SR, αSR) | 101–105 | C₂₂H₂₃Cl₂NO₅ | 58.42 (58.46 | 5.13 5.38 | 3.10 3.08) | a: $^1$H-NMR(CDCl₃) δ: 1.27(3H,t,J=7.2 Hz), 1.30(3H,d, j=7.0 Hz), 1.56(3H,d,J=6.8 Hz), 2.01 (1H,ddd,J=14.4,10.4, 4.0 Hz), 2.50 (1H,ddd,J=14.4,9.0,3.0 Hz), 2.99(1H,d,J=6.4 Hz), 4.22 (2H,q,J=7.2 Hz), 4.1–4.3(1H,m), 4.35–4.5(1H,m), 4.7–5.0(1H,m), 6.05(1H,s), 6.51(1H,d,J=2.4 Hz), 7.2–7.6 (6H,m)

b. $^1$H-NMR(CDCl₃) δ: 1.18(3H,t,J=7.1 Hz), 1.29(3H,d, J=7.0 Hz), 1.56(3H,d,J=6.8 Hz), 2.3–2.45(2H,m), 3.22(1H, d,J=4.5 Hz), 4.0–4.3(3H,m), 4.3–4.4(1H,m), 4.7–4.95(1H, m), 6.00(1H,s), 6.49(1H,d,J=2.2 Hz), 7.2–7.8(6H,m)

c: $^1$H-NMR(CDCL₃) δ: 0.93(3H,d,J=6.8 Hz), 1.03(3H,d, J=6.6 Hz), 1.26(3H,t,J=7.1 Hz), 1.85–2.1(1H,m), 2.52(1H, ddd,J=14.3,9.2,2.6 Hz), 2.9–3.05(1H,m), 3.42(1H,dd,J= 13.8,5.4 Hz), 4.05–4.55(4H,m), 6.18(1H,s), 6.52(1H,d,J=2.3 Hz), 7.2–7.85(6H,m)

d: $^1$H-NMR(CDCl₃) δ: 0.93(3H,d,J=6.8 Hz), 1.04(3H,d, J=6.6 Hz), 1.18(3H,t,J=7.1 Hz), 1.85–2.1(1H,m), 2.25–2.5 (2H,m), 3.1–3.3(1H,br), 3.43(1H,dd,J=13.6,5.4 Hz), 4.0–4.45(5H,m), 6.14(1H,s), 6.51(1H,d,J=2.2 Hz),7.2–7.8 (6H,m)

Physico-chemical properties of the intermediates (1) 3,5-trans-7-Chloro-(2-chlorophenyl)-1-isopropyl-2-oxo-1,2,3,5-tetrahydro-4,1-benzoxazepine-3-ethanol, m.p. 188°–189° C.

Elemental Analysis for C₂₀H₂₁Cl₂NO₃: Calcd.: C, 60.92; H, 5.37; N, 3.55 Found: C, 61.12; H, 5.39; N, 3.72

(2) 3,5-trans-7-Chloro-(2-chlorophenyl)-1-isopropyl-2-oxo-1,2,3,5-tetrahydro-4,1-benzoxazepine-3-acetaldehyde, an oily compound $^1$H-NMR(CDCl₃) δ: 1.30(3H,d,J=7.0 Hz), 1.56(3H,d,J= 6.6 Hz), 2.88(1H,ddd,J=17.6,5.4,1.6 Hz), 3.09(1H,ddd,J= 17.6,6.6,1.0 Hz), 4.37(1H,t,J=6.1 Hz),4.8– 5.0(1H,m), 6.02 (1H,s), 6.52(1H,d,J=2.4 Hz), 7.2–7.8(6H,m)

(3) 3,5-trans-7-Chloro-5-(2-chlorophenyl)-1-isobutyl-2-oxo-1,2,3,5-tetrahydro-4,1-benzoxazepine-3-ethanol, m.p. 147°–149° C.

Elemental Analysis for C₂₁H₂₃Cl₂NO₃: Calcd.: C, 61.77; H, 5.68; N, 3.43 Found: C, 61.64; H, 5.87; N, 3.54

(4) 3,5-trans-7-Chloro-5-(2-chlorophenyl)-1-isobutyl-2-oxo-1,2,3,5-tetrahydro-4,1-benzoxazepine-3-acetaldehyde, an oily compound $^1$H-NMR(CDCl₃) δ: 0.94(3H,d,J=6.8 Hz), 1.03(3H,d,J= 6.6 Hz), 1.85–2.1(1H,m), 2.90(1H,ddd,J=17.6,5.4,1.4 Hz), 3.12(1H,ddd,J=17.6,6.6,1.0 Hz), 3.45(1H,dd,J=13.8,5.6 Hz), 4.31(1H,dd,J=13.8,8.2 Hz), 4.4–4.55(1H,m), 6.15(1H, s), 6.54(1H,d,J=2.4 Hz), 7.2–7.8(6H,m), 9.84(1H,s)

Reference Example 1

3,5-trans-7-Chloro-5-(2-chlorophenyl)-1-isopropyl-2-oxo-1,2,3,5-tetrahydro-4,1-benzoxazepine-3-(β-hydroxy) butyric acid ethyl ester

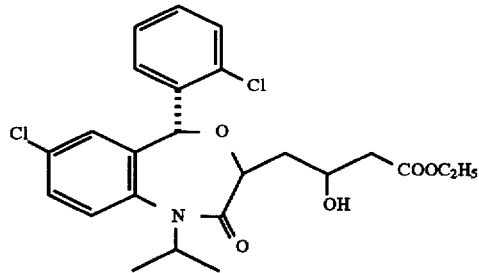

To a solution of diisopropylamine (0.70 ml)in dry tetrahydrofuran (5 ml)was added a hexane solution (3.03 ml, 1.64 mol/L)of n-butyllithium at temperatures ranging from −15° C. to −20° C. The mixture was stirred for one hour at the same temperature range. The reaction mixture was cooled to −78° C., to which was added acetic acid ethyl ester (0.49 ml), and the mixture was stirred for 15 minutes. To the reaction mixture was added dropwise for 5 minutes a dry tetrahydrofuran (10 ml) solution of 3,5-trans-7-chloro-5-(2-chlorophenyl)-1-isopropyl-2-oxo-1,2,3,5-tetrahydro-4,1-benzoxazepine-3-acetaldehyde. The mixture was stirred for 30 minutes, to which was added dilute hydrochloric acid (50 ml), followed by extraction with acetic acid ethyl ester. The organic layer was washed with a saturated aqueous solution of sodium hydrogencarbonate, which was dried over anhydrous magnesium sulfate. The solvent was distilled off, and the residue was purified by means of a silica gel column chromatography to afford colorless crystals (1.20 g), m.p. 119°–121° C.

Elemental Analysis for C₂₄H₂₇Cl₂NO₅: Calcd.: C, 60.01; H, 5.67; N, 2.92 Found: C, 60.16; H, 5.78; N, 2.97

Reference Example 2

3,5-trans-7-Chloro-5-(2-chlorophenyl)-1-isopropyl-2-oxo-1,2,3,5-tetrahydro-4,1-benzoxazepine-3-(β-hydroxy) butyric acid

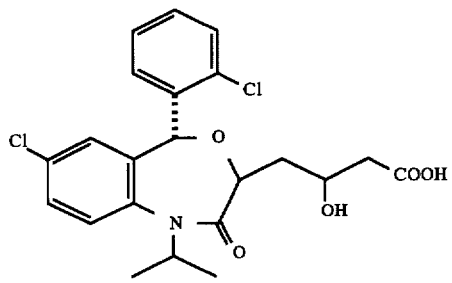

In substantially the same manner as in Example 15, a non-crystalline solid was obtained.

¹H-NMR(CDCl₃) δ: 1.29,1.30(3H,each d,J=7.0 Hz), 1.56, 1.57(3H,each d,J=6.8 Hz), 2.0–2.15(2H,m), 2.45–2.7(2H, m), 4.05–4.2(1H,m), 4.2–4.4(1H,m), 4.75–4.95(1H,m), 6.01 (1H,s), 6.45–6.55(1H,m), 7.2–7.8(6H,m)

Reference Example 3

(3RS,5SR,βRS)-7-chloro-5-(2-chlorophenyl)-1-isopropyl-2-oxo-1,2,3,5-tetrahydro-4,1-benzoxazepine-3-(β-hydroxy)ethanol

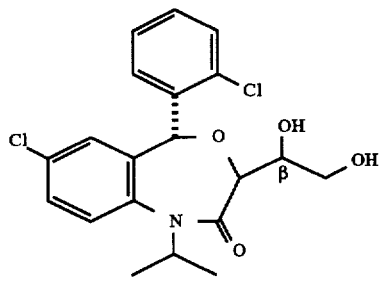

To a solution of (3RS,5SR,αSR)-7-chloro-5-(2-chlorophenyl)-1-isopropyl-2-oxo-1,2,3,5-tetrahydro-4,1-benzoxazepine-3-glycolic acid ethyl ester (1.0 g) in ethanol (30 ml) was added sodium borohydride (0.14 g). The mixture was stirred for 4 hours at room temperature. The reaction mixture was made acid with dilute hydrochloric acid, which was extracted with acetic acid ethyl ester. The extract solution was washed with a saturated aqueous solution of sodium hydrogencarbonate, which was dried over anhydrous magnesium sulfate. The solvent was distilled off, and the residue was purified by means of a silica gel column chromatography to give colorless crystals (0.62 g), m.p. 229°–230° C.

Elemental Analysis for $C_{20}H_{21}Cl_2NO_4$: Calcd.: C, 58.33; H, 5.16; N, 3.41 Found: C, 58.49; H, 5.21; N, 3.32

Reference Example 4

Using the compounds obtained in Example 14 and Example 17, by substantially the same manner as in Reference Example 3, the compounds shown in [Table 4] were obtained.

TABLE 4

| Compd. No. | R | Steric Configuration | |
|---|---|---|---|
| 1 | (CH₂)₂CH₃ | 3RS, 5SR, βRS | oily |
| | ¹HNMR(CDCl₃)δ: 0.97(3H, t, J=7.3Hz), 1.5–1.9(2H, m), 2.0–2.3(3H, m), 2.82(1H, br), 3.4–3.75(3H, m), 3.8–4.05 (1H, m), 4.18(1H, t, J=6.4Hz), 4.3–4.5(1H, ddd, J=12.6, 9.8, 6.4Hz), 6.04(1H, s), 6.52(1H, d, J=2.2Hz), 7.2–7.8 (6H, m) | | |
| 2 | (CH₂)₂CH₃ | 3RS, 5SR, βSR | oily |
| | ¹HNMR(CDCl₃)δ: 0.97(3H, t, J=7.4Hz), 1.5–1.9(2H, s), 2.0–2.3(3H, m), 3.4–3.8(3H, m), 3.9–4.05(1H, m), 4.20 (1H, t, J=5.7Hz), 4.3–4.5(1H, ddd, J=12.6, 9.8, 6.4Hz), 6.03(1H, s), 6.53(1H, d, J=2.2Hz), 7.2–7.8(6H, m) | | |
| 3 | CH₂CH(CH₂)₂ | 3RS, 5SR, βRS | oily |
| | ¹HNMR(CDCl₃)δ: 0.93(3H, d, J=6.6Hz), 1.03(3H, d, J= 6.6Hz), 1.8–2.15(3H, m), 3.35–3.75(3H, m), 3.85–4.05 (1H, m), 4.19(1H, t, J=6.4Hz), 4.33(1H, dd, J=13.6, 8.4Hz), 6.14(1H, s), 6.52(1H, d, J=2.2Hz), 7.2–7.8(6H, m) | | |

Reference Example 5

3,5-trans-7-Chloro-5-(2-chlorophenyl)-1-isopropyl-2-oxo-1,2,3,5-tetrahydro-4,1-benzoxazepine-3-(γ-hydroxy) butanol

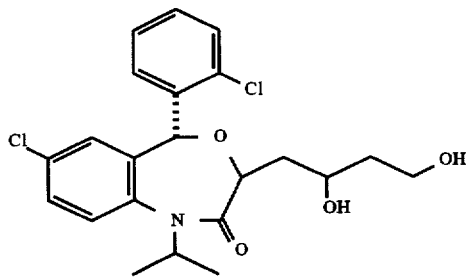

By subjecting the compound obtained in Reference Example 1 to substantially the same procedure as in Reference Example 3, a non-crystalline solid compound was obtained.

¹H-NMR(CDCl₃) δ: 1.30(3H,d,J=7.0 Hz), 1.56(3H,d,J= 6.6 Hz), 1.6–1.9(2H,m), 2.0–2.2(2H,m), 3.8–3.95(2H,m), 4.0–4.2(2H,m), 4.75–4.95(1H,m), 6.02(1H,s), 6.5–6.6(1H, m), 7.2–7.8(6H,m)

Example 18

N-[(3RS,5SR,αSR)-7-Chloro-5-(2-chlorophenyl)-1-isopropyl-2-oxo-1,2,3,5-tetrahydro-4,1-benzoxazepine-3-glycolyl]aminoacetic acid ethyl ester

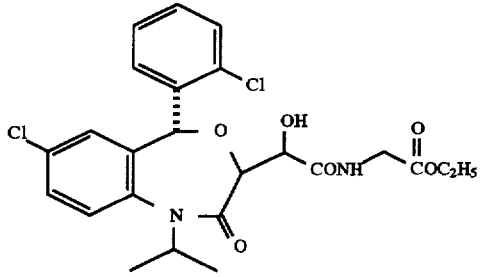

In N-dimethylformamide (10 ml) were dissolved (3RS,5SR,αSR)-7-chloro-5-(2-chlorophenyl)-1-isopropyl-2-oxo-1,2,3,5-tetrahydro-4,1-benzoxazepine-3-glycolic acid (0.3 g) obtained in Example 1 and glycine ethyl ester hydrochloride (0.12 g). To the solution were added diethyl cyanophosphonate (0.15 g) and triethylamine (0.24 ml) under ice-cooling. The mixture was stirred for 30 minutes at room temperature, which was subjected to extraction by the addition of water (100 ml) and ethyl acetate (100 ml). The ethyl acetate layer was washed with 1N hydrochloric acid and an aqueous solution of sodium hydrogencarbonate, which was then dried over anhydrous magnesium sulfate, followed by distilling off the solvent under reduced pressure. The residue was purified by means of a silica gel column chromatography (hexane:ethyl acetate=1:1) to afford N-[(3RS,5SR,αSR)-7-chloro-5-(2-chlorophenyl)-1-isopropyl-2-oxo-1,2,3,5-tetrahydro-4,1-benzoxazepine-3-glycolyl]aminoacetic acid ethyl ester (0.30 g) as prisms, m.p. 157°–159° C.

Elemental Analysis for $C_{24}H_{26}Cl_2N_2O_6$: Calcd.: C, 56.59; H, 5.14; N, 5.50 Found: C, 56.60; H, 5.21; N, 5.52

Example 19

N-[(3RS,5SR,αSR)-7-Chloro-5-(2-chlorophenyl)-1-isopropyl-2-oxo-1,2,3,5-tetrahydro-4,1-benzoxazepine-3-glycolyl]aminoacetic acid

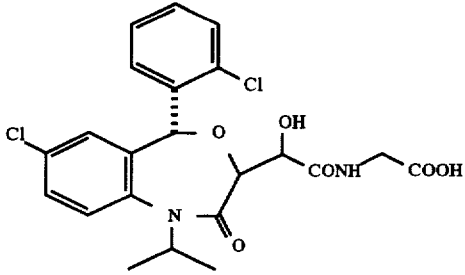

In ethanol (10 ml) was dissolved N-[(3RS,5SR,αSR)-7-chloro-5-(2-chlorophenyl)-1-isopropyl-2-oxo-1,2,3,5-tetrahydro-4,1-benzoxazepine-3-glycolyl]aminoacetic acid ethyl ester (0.2 g). To the solution was added 1N sodium hydroxide aqueous solution (2 ml), which was stirred for 15 minutes. To the mixture was added 1N hydrochloric acid (100 ml) to make the solution acid, followed by extraction with ethyl acetate (100 ml). The ethyl acetate layer was washed with water, then dried over anhydrous magnesium sulfate, followed by distilling off the solvent under reduced pressure to afford N-[(3RS,5SR,αSR)-7-chloro-5-(2-chlorophenyl)-1-isopropyl-2-oxo-1,2,3,5-tetrahydro-4,1-benzoxazepine-3-glycolyl]aminoacetic acid (0.18 g) as crystals, m.p. 142°–145° C.

Elemental Analysis for $C_{22}H_{22}Cl_2N_2O_6 \cdot 1/4H_2O$: Calcd.: C, 54.39; H, 4.66; N, 5.77 Found: C, 54.29; H, 4.61; N, 5.77

Example 20

N-[(E)-7-chloro-5-(2-chlorophenyl)-1-isopropyl-2-oxo-1,2,3,5-tetrahydro-4,1-benzoxazepine-Δ(3,α)-acetyl]aminoacetic acid ethyl ester

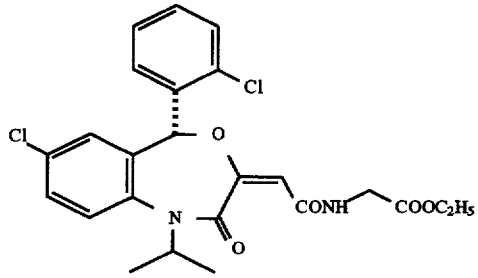

To a solution of (E)-7-chloro-5-(2-chlorophenyl)-1-isopropyl-2-oxo-1,2,3,5-tetrahydro-4,1-benzoxazepine-Δ(3,α)-acetyl]aminoacetic acid (0.3 g) and glycine ethyl ester hydrochloride (0.124 g) in dimethylformamide (10 ml) were added diethyl cyanophosphonate (0.152 g) and triethylamine (0.25 ml). The mixture was stirred for 30 minutes at room temperature. To the reaction mixture was addled acetic acid ethyl ester, which was washed with dilute hydrochloric acid and a saturated aqueous solution of sodium hydrogencarbonate, then the solvent was distilled off. The residue was purified by means of a silica gel column chromatography to yield colorless crystals (0.35 g), m.p. 207°–208° C.

Elemental Analysis for $C_{24}H_{24}Cl_2N_2O_5$: Calcd.: C, 58.67; H, 4.92; N, 5.70 Found: C, 58.62; H, 4.97; N, 5.68

Example 21

N-[(E)-7-Chloro-5-(2-chlorophenyl)-1-isopropyl-2-oxo-1,2,3,5-tetrahydro-4,1-benzoxazepine-Δ(3,α)-acetyl)aminoacetic acid

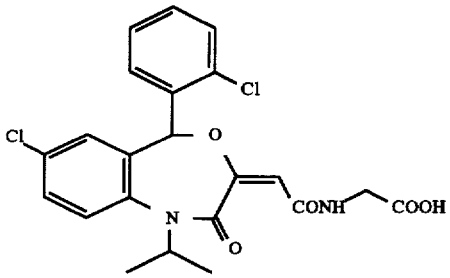

To a solution of the compound (0.25 g) obtained in Example 20 in ethanol (20 ml) was added a 1N aqueous solution of sodium hydroxide (4 ml). The mixture was stirred for 30 minutes at room temperature. The reaction mixture was made acid with dilute hydrochloric acid, which was extracted with acetic acid ethyl ester. The extract was washed with water and dried over anhydrous magnesium sulfate. The solvent was distilled off, and the residue was recrystallized from hexane to give colorless crystals (0.21 g), m.p. 217°–221° C. (decomp.)

Elemental Analysis for $C_{22}H_{20}Cl_2N_2O_5 \cdot 0.5H_2O$: Calcd.: 55.94; H, 4.48; N, 5.93 Found: 56.17; H, 4.60; N, 6.05

Example 22

Starting from the compound obtained in Example 13, the compounds shown in [Table 5] were obtained by substantially the same procedures as in Example 25 and Example 26.

TABLE 5

| Compd. No. | $R_1$ | $R_2$ | m.p. (°C.) | Molecular Formula | Elemental Analysis (Found) | | |
|---|---|---|---|---|---|---|---|
| | | | | | C | H | N |
| 1 | $(CH_2)_2CH_3$ | $C_2H_5$ | 203–205 | $C_{24}H_{24}Cl_2N_2O_5$ | 58.67 (58.48 | 4.98 5.08 | 5.70 5.64) |
| 2 | $(CH_2)_2CH_3$ | H | 210–213 (decomp.) | $C_{22}H_{20}Cl_2N_2O_5$ | 57.03 (56.95 | 4.35 4.41 | 6.05 6.23) |
| 3 | $CH_2CH(CH_3)_2$ | $C_2H_5$ | 182–185 | $C_{25}H_{26}Cl_2N_2O_5$ | 59.41 (58.90 | 5.19 5.17 | 5.54 5.56) |
| 4 | $CH_2CH(CH_3)_2$ | H | 219–221 (decomp.) | $C_{23}H_{22}Cl_2N_2O_5$ | 57.87 (57.57 | 4.65 4.73 | 5.87 5.95) |

Assay Method of Squalene Synthetase Inhibitory Activity

The squalene synthetase inhibitory activity was assayed as follows with the enzyme solutions described in the subsequent Experimental Examples 1 and 2.

More specifically, an enzyme solution (protein content 0.8 ug) prepared in Experimental Example 1 or 2 was added to a solution (total volume 50 µl)) containing 5 µM [1-$^3$H] farnesyl pyrophosphate (specific activity 25 µCi/mole), 1 mM NADPH, 5 mM $MgCl_2$, 6 mM glutathione, a 100 mM buffer solution of potassium phosphate (pH 7.4) and a test drug (used as an aqueous solution or a DMSO solution), then the reaction was allowed to proceed at 37° C. for 45 minutes. To the reaction mixture was added 150 µl of a mixture of chloroform and methanol (1:2) to suspend the reaction, followed by adding 50 µl of chloroform and 50 µl of a 3N aqueous solution of sodium hydroxide. 50 µl of the chloroform layer (lower layer) containing the reaction mixture having squalene as the principal component and 3 ml of toluene-based liquid scintillator were mixed, and its radioactivity was determined by means of a liquid scintillation counter.

The squalene synthetase inhibitory activity was expressed in terms of the concentration inhibiting by 50% the radioactivity taken into the chloroform layer ($IC_{50}$, molar concentration (M)).

Experimental Example 1

Preparation of rat-derived enzyme

An SD male rat (6 week old) was killed by bleeding, and its liver was excised. About 10 g of the liver was washed with a saline solution cooled with ice, which was then homogenized in 15 ml of an ice-cooled buffer solution [100 mM potassium phosphate (pH 7.4), 15 mM nicotinamide, 2 mM $MgCl_2$], followed by centrifugation for 20 minutes (4° C.) with 10000×g. The supernatant layer was separated and subjected to further centrifugation for 90 minutes (4° C.) at 105000×g. The sediment was then suspended in an ice-cooled 100 mM phosphate buffer solution (pH 7.4), which was again subjected to centrifugation for 90 minutes (4° C.) at 105000×g. The sediment thus obtained (microsome fraction) was suspended in an ice-cooled 100 mM potassium phosphate buffer (pH 7.4) (about 40 mg/ml protein concentration, determined with BCA protein assay kit of Pias Co., Ltd.). This suspension was used as the enzyme solution.

Experimental Example 2

Preparation of human-derived enzyme

Human hepatic carcinoma cells HepG2 (about 1×10$^9$ cells) obtained by incubation in a Dulbecco-modified Eagle's medium (37° C. in the presence of 5% $CO_2$) were suspended in 10 ml of an ice-cooled buffer solution [100 mM potassium phosphate buffer (pH 7.4), 30 mM nicotinamide and 2.5 mM $MgCl_2$]. The cells were crushed by means of ultrasonication (for 30 seconds, twice). From the sonicate thus obtained, the microsome fraction was obtained by the same procedure as in Experiment Example 1, which was suspended in an ice-cooled 100 mM potassium phosphate buffer (pH 7.4) (about 4 mg/ml protein concentration). This suspension was used as the enzyme solution. The results are shown in [Table 6].

TABLE 6

| Compd. No. | Rat-derived enzyme ($10^{-7}$M) | Human-derived enzyme ($10^{-7}$M) |
|---|---|---|
| Example | | |
| 12 | 3.1 | |
| 13-4 | 0.76 | |
| 13-8 | 3.6 | |
| 15 | 2.4 | |

TABLE 6-continued

| Compd. No. | Rat-derived enzyme ($10^{-7}$M) | Human-derived enzyme ($10^{-7}$M) |
|---|---|---|
| 16 | 2.8 | |
| 17-5 | 5.3 | |
| 17-6 | 6.0 | |
| 17-7 | 2.3 | |
| 17-8 | 3.3 | |
| 21 | 1.9 | |
| 22-2 | 1.3 | |
| 22-4 | 0.98 | 0.47 |
| R. Ex. | | |
| 3 | 9.9 | |
| 4-1 | 9.7 | |
| 4-2 | 8.8 | |

Formulation Examples

A squalene synthetase inhibiting agents containing, as its effective component, a condensed 7-membered compound represented by the formula (I) of this invention or a salt thereof, in the case where it is used as a therapeutic agent of hypercholesteremia, can be formulated in accordance with, for example, the following prescriptions.

| 1. Capsules | |
|---|---|
| (1) Compound obtained in Example 13-4 | 10 mg |
| (2) Lactose | 90 mg |
| (3) Microcrystalline cellulose | |
| (4) Magnesium stearate | 70 mg |
| One capsule | 180 mg |

(1), (2) and (3) and one half of (4) were blended and the mixture was granulated, to which was added the balance of (4). The mixture was filled in a gelatin capsule.

| 2. Tablets | |
|---|---|
| (1) Compound obtained in Example 13-4 | 10 mg |
| (2) Lactose | 35 mg |
| (3) Corn starch | 150 mg |
| (4) Microcrystalline cellulose | 30 mg |
| (5) Magnesium stearate | 5 mg |
| One tablet | 230 mg |

(1), (2) and (3) and two thirds of (4) and one half of (5) were blended and the mixture was granulated, to which were added the balance of (4) and (5). The mixture was subjected to compression-molding to provide tablets.

| 3. Injections | |
|---|---|
| (1) Sodium salt of the compound obtained in Example 13-4 | 10 mg |
| (2) Inositol | 100 mg |
| (3) Benzyl alcohol | 20 mg |
| One ampoule | 130 mg |

(1), (2) and (3) were dissolved in distilled water for injection to make the whole volume 2 ml, which was put in an ampoule, and the ampoule was sealed. All the processes were conducted under sterilized conditions.

| 4. Capsules | |
|---|---|
| (1) Compound obtained in Example 22-4 | 10 mg |
| (2) Lactose | 90 mg |
| (3) Microcrystalline cellulose | 70 mg |
| (4) Magnesium stearate | 10 mg |
| One capsule | 180 mg |

(1), (2) and (3) and one half of (4) were blended and the mixture was granulated, to which was added the balance of (4). The mixture was filled in a gelatin capsule.

| 5. Tablets | |
|---|---|
| (1) Compound obtained in Example 22-4 | 10 mg |
| (2) Lactose | 35 mg |
| (3) Corn starch | 150 mg |
| (4) Microcrystalline cellulose | 30 mg |
| (5) Magnesium stearate | 5 mg |
| One tablet | 230 mg |

(1), (2) and (3) and two thirds of (4) and one half of (5) were blended and the mixture was granulated, to which were added the balance of (4) and (5). The mixture was subjected to compression-molding to provide tablets.

| 6. Injections | |
|---|---|
| (1) Sodium salt of the compound obtained in Example 22-4 | 10 mg |
| (2) Inositol | 100 mg |
| (3) Benzyl alcohol | 20 mg |
| One ampoule | 130 mg |

(1), (2) and (3) were dissolved in distilled water for injection to make the whole volume 2 ml, which was put in an ampoule, and the ampoule was sealed. All the processes were conducted under sterilized conditions.

What is claimed is:

1. A compound represented by the formula (I)

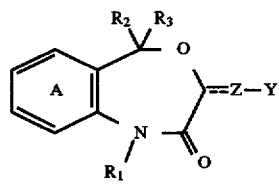

wherein $R_1$ stands for H or a hydrocarbon group which may be substituted by one to five substituents selected from the group consisting of
(1) phenyl, naphthyl, anthryl, phenanthryl, or acenaphthylenyl which may be substituted by one or two substituents selected from the group consisting of (i) $C_{1-3}$ alkoxy groups, (ii) halogen atoms and, (iii) $C_{1-3}$ alkyl groups,
(2) $C_{3-7}$ cycloalkyl groups which may be substituted by one or two substituents selected from the group consisting of (i) $C_{1-3}$ alkoxy groups, (ii) halogen atoms, and (iii) $C_{1-3}$ alkyl groups,
(3) $C_{3-6}$ cycloalkenyl groups which may be substituted by one or two substituents selected from the group consisting of (i) $C_{3-6}$ alkoxy groups, (ii) halogen atoms, and (iii) $C_{1-3}$ alkyl groups,
(4) furyl, thienyl, pyrrolyl, oxazolyl, isoxazolyl, thiazolyl, isothiazolyl, imidazolyl, pyrazolyl, 1,2,3- oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, triazinyl, benzofuranyl, isobenzofuranyl, benzo[b]thienyl, indolyl, isoindolyl, 1H-indazolyl, benzimidazolyl, benzoxazolyl, 1,2-benzoisoxazolyl, benzothiazolyl, 1,2-benzoisothiazolyl, 1H-benzotriazolyl, quinolyl, isoquinolyl, cinnolinyl, quinazolinyl, quinoxalinyl, phthalazinyl, naphthyridinyl, purinyl, pteridinyl, carbazolyl, α-carbolinyl, β-carbolinyl, γ-carbolinyl, acrydinyl, phenoxazinyl, phenothiazinyl, phenazinyl, phenoxathiinyl, thianthrenyl, phenanthridinyl, phenanthrolinyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, 1,2,4-triazolo[4,3-b]pyridazinyl, oxiranyl, azetidinyl, oxetanyl, thietanyl, pyrrolidinyl, tetrahydrofuryl, thiolanyl, piperidyl, tetrahydropyranyl, morpholinyl, thiomorpholinyl, or piperazinyl which may be substituted by $C_{1-3}$ alkyl groups, (5) amino groups which may be substituted by $C_{1-3}$ alkyl group(s), (6) hydroxy groups which may be substituted by a $C_{1-3}$ alkyl group, (7) thiol groups which may be substituted by a $C_{1-3}$ alkyl group, and (8) halogens;

$R_2$ and $R_3$ independently stand for H, an alkyl group which may be substituted by substituents selected from the group consisting of (1) halogen atoms and (2) $C_{1-4}$ lower alkoxy groups, a phenyl group which may be substituted by 1 to 3 substituents selected from the group consisting of (1) halogen atoms, (2) $C_{1-4}$ alkyl groups which may be substituted by 1 to 5 halogen atoms, (3) $C_{1-4}$ alkoxy groups which may be substituted by 1 to 5 halogen atoms, (4) hydroxyl groups which may be substituted by a substituent selected from the group consisting of (i) $C_{1-4}$ alkyl groups, (ii) $C_{3-6}$ cycloalkyl groups, (iii) phenyl, 1-naphthyl or 2-naphthyl, and (iv) benzyl or phenethyl, (5) nitro group and (6) cyano group;

or furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, triazinyl, benzofuranyl, isobenzofuranyl, benzo[b]thienyl, indolyl, isoindolyl, 1H-indazolyl, benzimidazolyl, benzoxazolyl, 1,2-benzoisoxazolyl, benzothiazolyl, 1,2-benzoisothiazolyl, 1H-benzotriazolyl, quinolyl, isoquinolyl, cinnolinyl, quinazolinyl, quinoxalinyl, phthalazinyl, naphthyridinyl, purinyl, pteridinyl, carbazolyl, α-carbolinyl, β-carbolinyl, γ-carbolinyl, acrydinyl, phenoxazinyl, phenothiazinyl, phenazinyl, phenoxathiinyl, thianthrenyl, phenanthridinyl, phenanthrolinyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, or 1,2,4-triazolo[4,3-b]pyridazinyl, which may be substituted by $C_{1-3}$ alkyl groups;

Z stands for methine, vinylene, propenylene, butenylene, butadienylene, methylpropenylene, ethylbutenylene, propylbutenylene, methylbutadienylene, ethylbutadienylene, propylbutadienylene, pentenylene, hexenylene, heptenylene, pentadienylene, hexadienylene, heptadienylene, or —Z'—CH(OH)—(Z' stands for a bond or a straight-chain or branched $C_{1-6}$ alkylene group);

the symbol ====== stands for a double bond or a single bond;

Y stands for an optionally esterified carboxyl group, a carbamoyl group which may be substituted by one or two of substituents selected from the group consisting of (1) lower ($C_{1-6}$) alkyl groups which may be substituted by 1to 3 substituents selected from the group consisting of (i) carboxyl group which may be esterified by a lower ($C_{1-5}$) alkyl group, (ii) furyl, thienyl, indolyl, isoindolyl, pyrazinyl, pyridyl, pyrimidyl or imidazolyl, (iii) amino group, (iv) hydroxyl group and (v) phenyl group, (2) $C_{3-6}$ cycloalkyl groups which may be substituted by 1 to 3 substituents selected from the group consisting of (i) carboxyl groups which may be esterified by a lower ($C_{1-5}$) alkyl group, (ii) furyl, thienyl, indolyl, isoindolyl, pyrazinyl, pyridyl, pyrimidyl or imidazolyl, (iii) amino group, (iv) hydroxyl group and (v) phenyl group, (3) phenyl, 1-naphthyl, or 2-naphthyl which may be substituted by substituents selected from the group consisting of (i) halogen atoms and (ii) carboxyl groups which may be esterified by a lower ($C_{1-4}$) alkyl group, (4) benzyl or phenethyl which may be substituted by the substituents selected from the group consisting of (i) halogen atoms and (ii) carboxyl groups which may be esterified by a $C_{1-4}$ alkyl group, or two substituents on the nitrogen atom of the carbamoyl group may form, together with the nitrogen atom, a cyclic amino group selected from the group consisting of (1) 1-azetidinyl, (2) 1-pyrrolidinyl, (3) piperidino, (4) morpholino and (5) 1-piperazinyl;

a hydroxyl group which may be substituted by a substituent selected from the group consisting of (1) $C_{1-4}$ alkyl groups, (2) $C_{3-6}$ cycloalkyl groups or (3) phenyl, 1-naphthyl or 2-naphthyl which may be substituted by substituents selected from the group consisting of (i) halogen atoms and (ii) carboxyl groups which may be esterified by a $C_{1-4}$ alkyl group, or (4) benzyl or phenethyl which may be substituted by substituents selected from the group consisting of (i) halogen atoms and (ii) carboxyl groups which may be esterified by a $C_{1-4}$ alkyl group, an amino group which may be substituted by substituents selected from the group consisting of (1) $C_{1-4}$ alkyl groups, (2) $C_{3-6}$ cycloalkyl groups, (3) phenyl, 1-naphthyl or 2-naphthyl which may be substituted by substituents selected from the group consisting of (i) halogen atoms and (ii) carboxyl group which may be esterified by $C_{1-4}$ alkyl group, (4) benzyl or phenethyl which may be substituted by the substituents selected from the group consisting of (i) halogen atoms and (ii) carboxyl group which may be esterified by $C_{1-4}$ alkyl group, or two substituents on the nitrogen atom of the amino group may form, together with the nitrogen atom, a cyclic amino group selected from the groups consisting of (1) 1-azetidinyl, (2) 1-pyrrolidinyl, (3) piperidino, (4) morpholino and (5) 1-piperazinyl;

and wherein the ring A may be substituted by one or two substituents selected from the group consisting of
(1) hydroxyl group,
(2) halogens,
(3) nitro group,
(4) cyano group,
(5) $C_{1-4}$ alkyl groups, and
(6) $C_{1-4}$ alkoxy groups, or a pharmaceutically acceptable salt thereof.

2. The compound or the salt thereof as claimed in claim 1, wherein $R_1$ is an aliphatic chain hydrocarbon group.

3. The compound or the salt thereof as claimed in claim 2, wherein $R_1$ is an alkyl group.

4. The compound or the salt thereof as claimed in claim 3, wherein $R_1$ is a lower alkyl group.

5. The compound or the salt thereof as claimed in claim 1, wherein $R_2$ or $R_3$ is a phenyl group, which may be substituted by 1 to 3 substituents selected from the group consisting of (1) halogen atoms,
(2) $C_{1-4}$ alkyl groups which may be substituted by one to five halogen atoms,
(3) $C_{1-4}$ alkoxy groups which may be substituted by one to five halogen atoms,
(4) hydroxyl groups which may be substituted by a substituent selected from the group consisting of (i) $C_{1-4}$ alkyl groups, (ii) $C_{3-6}$ cycloalkyl groups, (iii) phenyl, 1-naphthyl or 2-naphthyl and (iv) benzyl or phenethyl,
(5) nitro groups and
(6) cyano groups.

6. The compound or the salt thereof as claimed in claim 1, wherein Z is a $C_{1-4}$ alkenyl group.

7. The compound or the salt thereof as claimed in claim 1, in which Y is an optionally esterified carboxyl group or a carbamoyl group which may be substituted by one or two of substituents selected from the group consisting of (1) lower ($C_{1-6}$) alkyl groups which may be substituted by 1 to 3 substituents selected from the group consisting of (i) carboxyl groups which may be esterified by a lower ($C_{1-5}$) alkyl group, (ii) furyl, thienyl, indolyl, isoindolyl, pyrazinyl, pyridyl, pyrimidyl or imidazolyl, (iii) amino group, (iv) hydroxyl group and (v) phenyl group, (2) $C_{3-6}$ cycloalkyl groups which may be substituted by 1 to 3 substituents selected from the group consisting of (i) carboxyl groups which may be esterified by a lower ($C_{1-5}$) alkyl group, (ii) furyl, thienyl, indolyl, isoindolyl, pyrazinyl, pyridyl, pyrimidyl or imidazolyl, (iii) amino group, (iv) hydroxyl group and (v) phenyl group, (3) phenyl, 1-naphthyl, or 2-naphthyl which may be substituted by substituents selected from the group consisting of (i) halogen atoms and (ii) carboxyl groups which may be esterified by a lower ($C_{1-4}$) alkyl group, and (4) benzyl or phenethyl which may be substituted by substituents selected from the group consisting of (i) halogen atoms and (ii) carboxyl groups which may be esterified by a lower ($C_{1-4}$) alkyl group, or two substituents on a nitrogen atom may form a cyclic amino group selected from a the group consisting of (1) 1-azetidinyl, (2) 1-pyrrolidinyl, (3) piperidino, (4) morpholino and (5) 1-piperazinyl.

8. The compound or the salt thereof as claimed in claim 1, in which the symbol ═══ is a double bond.

9. A squalene synthetase inhibitor which comprises the compound or a salt thereof as claimed in claim 1 and a pharmaceutically acceptable carrier.

10. A compound as claimed in claim 1 which is (3RS, 5SR,αRS)-7-chloro-5-(2-chlorophenyl)-1-isobutyl-2-oxo-1,2,3,5-tetrahydro-4,1-benzoxazepine-3-(α-hydroxy) propionic acid or a pharmaceutically acceptable salt thereof.

11. A compound as claimed in claim 1 which is (3RS, 5SR,αSR)-7-chloro-5-(2-chlorophenyl)-1-isobutyl-2-oxo-1,2,3,5-tetrahydro-4,1-benzoxazepine-3-(α-hydroxy) propionic acid or a pharmaceutically acceptable salt thereof.

12. A compound as claimed in claim 1, which is (3RS, 5SR,αSR)-7-chloro-5-(2-chlorophenyl)-1-isopropyl-2-oxo-1,2,3,5-tetrahydro-4,1-benzoxazepine-3-glycolic acid or a pharmaceutically acceptable salt thereof.

13. A compound as claimed in claim 1, which is (3RS, 5RS,αSR)-7-chloro-5-(2-chlorophenyl)-1-isopropyl-2-oxo-1,2,3,5-tetrahydro-4,1-benzoxazepine-3-glycolic acid or a pharmaceutically acceptable salt thereof.

14. A compound as claimed in claim 1, which is (3RS, 5RS,αRS)-7-chloro-5-(2-chlorophenyl)-1-isopropyl-2-oxo-1,2,3,5-tetrahydro-4,1-benzoxazepine-3-glycolic acid or a pharmaceutically acceptable salt thereof.

15. A compound as claimed in claim 1, which is (3RS, 5SR,αRS)-7-chloro-5-(2-chlorophenyl)-1-isopropyl-2-oxo-1,2,3,5-tetrahydro-4,1-benzoxazepine-3-glycolic acid or a pharmaceutically acceptable salt thereof.

16. A compound as claimed in claim 1, which is (Z)-7-chloro-5-(2-chlorophenyl)-1-isopropyl-2-oxo-1,2,3,5-tetrahydro-4,1-benzoxazepine-3-Δ(3,α)-acetic acid or a pharmaceutically acceptable salt thereof.

17. A compound as claimed in claim 1, which is (E)-7-chloro-5-(2-chlorophenyl)-1-isopropyl-2-oxo-1,2,3,5-tetrahydro-4,1-benzoxazepine-3-Δ(3,α)-acetic acid or a pharmaceutically acceptable salt thereof.

18. A compound as claimed in claim 1, which is (Z)-7-chloro-5-(2-chlorophenyl)-2-oxo-1-propyl-1,2,3,5-tetrahydro-4,1-benzoxazepine-3-Δ(3,α)-acetic acid or a pharmaceutically acceptable salt thereof.

19. A compound as claimed in claim 1, which is (E)-7-chloro-5-(2-chlorophenyl)-2-oxo-1-propyl-1,2,3,5-tetrahydro-4,1-benzoxazepine-3-Δ(3,α)-acetic acid or a pharmaceutically acceptable salt thereof.

20. A compound as claimed in claim 1, which is (Z)-7-chloro-5-(2-chlorophenyl)-1-isobutyl-2-oxo-1,2,3,5-tetrahydro-4,1-benzoxazepine-3-Δ(3,α)-acetic acid or a pharmaceutically acceptable salt thereof.

21. A compound as claimed in claim 1, which is (E)-7-chloro-5-(2-chlorophenyl)-1-isobutyl-2-oxo-1,2,3,5-tetrahydro-4,1-benzoxazepine-3-α(3,α)-acetic acid or a pharmaceutically acceptable salt thereof.

22. A compound as claimed in claim 1, which is (3RS, 5SR,αRS)-7-chloro-5-(2-chlorophenyl)-2-oxo-1-propyl-1,2,3,5-tetrahydro-4,1-benzoxazepine-3-(α-hydroxy) propionic acid or a pharmaceutically acceptable salt thereof.

23. A compound as claimed an claim 1, which is (3RS, 5SR,αSR)-7-chloro-5-(2-chlorophenyl)-2-oxo-1-propyl-1,2,3,5-tetrahydro-4,1-benzoxazepine-3-(α-hydroxy) propionic acid or a pharmaceutically acceptable salt thereof.

24. A compound as claimed in claim 1, which is (3RS, 5SR,αRS)-7-chloro-5-(2-chlorophenyl)-1-isopropyl-2-oxo-1,2,3,5-tetrahydro-4,1-benzoxazepine-3-(α-hydroxy) propionic acid or a pharmaceutically acceptable salt thereof.

25. A compound as claimed an claim 1, which is (3RS, 5SR,αSR)-7-chloro-5-(2-chlorophenyl)-1-isopropyl-2-oxo-1,2,3,5-tetrahydro-4,1-benzoxazepine-3-(α-hydroxy) propionic acid or a pharmaceutically acceptable salt thereof.

* * * * *